United States Patent
Brady et al.

(10) Patent No.: US 9,084,674 B2
(45) Date of Patent: Jul. 21, 2015

(54) INTRAOCULAR LENS WITH SHAPE CHANGING CAPABILITY TO PROVIDE ENHANCED ACCOMODATION AND VISUAL ACUITY

(75) Inventors: Daniel G. Brady, San Juan Capistrano, CA (US); Huawei Zhao, Irvine, CA (US); Edward Geraghty, Rancho Santa Margarita, CA (US); Scott J. Catlin, Orange, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 199 days.

(21) Appl. No.: 13/462,114

(22) Filed: May 2, 2012

(65) Prior Publication Data

US 2013/0297018 A1 Nov. 7, 2013

(51) Int. Cl.
*A61F 2/16* (2006.01)

(52) U.S. Cl.
CPC ............. *A61F 2/1635* (2013.01); *A61F 2/1624* (2013.01); *A61F 2/1618* (2013.01); *A61F 2002/1681* (2013.01); *A61F 2002/1689* (2013.01); *A61F 2250/0018* (2013.01)

(58) Field of Classification Search
CPC ....... A61F 2/16; A61F 2/1613; A61F 2/1618; A61F 2/1624; A61F 2/1635; A61F 2/1648; A61F 2/1681; A61F 2250/0053
USPC ............. 623/6.24, 6.27–6.29, 6.37, 6.39–6.4, 623/6.46, 6.49, 6.33
See application file for complete search history.

(56) References Cited

U.S. PATENT DOCUMENTS

| | | |
|---|---|---|
| 4,361,913 A | 12/1982 | Streck |
| 4,370,760 A | 2/1983 | Kelman |
| 4,373,218 A | 2/1983 | Schachar |
| 4,442,553 A | 4/1984 | Hessburg |
| 4,512,040 A | 4/1985 | McClure |
| 4,560,383 A | 12/1985 | Leiske |
| 4,562,600 A | 1/1986 | Ginsberg et al. |
| 4,615,701 A | 10/1986 | Woods |
| 4,641,934 A | 2/1987 | Freeman |
| 4,731,078 A | 3/1988 | Stoy et al. |
| 4,769,035 A | 9/1988 | Kelman |
| 4,813,955 A | 3/1989 | Achatz et al. |
| 4,842,601 A | 6/1989 | Smith |

(Continued)

FOREIGN PATENT DOCUMENTS

| | | |
|---|---|---|
| CH | 681687 A5 | 5/1993 |
| EP | 766540 A1 | 4/1997 |

(Continued)

OTHER PUBLICATIONS

International Search Report and Written Opinion for Application No. PCT/US2013/039302, mailed on Jul. 26, 2013, 9 pages.

(Continued)

*Primary Examiner* — Howie Matthews
(74) *Attorney, Agent, or Firm* — Abbott Medical Optics Inc.

(57) ABSTRACT

An intraocular lens for providing a range of accommodative vision, an extended depth of focus, or enhanced performance through the asymmetric transfer of ocular forces to the lens. The intraocular lens contains an optic and a haptic. The shape and/or material of the haptic results in the transmission of ocular forces to particular regions in the optic. Greater forces applied to particular regions result in deformation of that region and increased power.

10 Claims, 17 Drawing Sheets

(56) References Cited

U.S. PATENT DOCUMENTS

| | | |
|---|---|---|
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,963,148 A | 10/1990 | Sulc et al. |
| 4,994,082 A | 2/1991 | Richards et al. |
| 4,994,083 A | 2/1991 | Sulc et al. |
| 5,047,051 A | 9/1991 | Cumming |
| 5,089,024 A | 2/1992 | Christie et al. |
| 5,152,789 A | 10/1992 | Willis |
| 5,275,623 A | 1/1994 | Sarfarazi |
| 5,476,514 A | 12/1995 | Cumming |
| 5,489,302 A | 2/1996 | Skottun |
| 5,496,366 A | 3/1996 | Cumming |
| 5,607,472 A | 3/1997 | Thompson |
| 5,628,795 A | 5/1997 | Langerman |
| 5,674,282 A | 10/1997 | Cumming |
| 5,800,532 A | 9/1998 | Lieberman |
| 5,984,962 A | 11/1999 | Anello et al. |
| 6,013,101 A | 1/2000 | Israel |
| 6,051,024 A | 4/2000 | Cumming |
| 6,083,261 A | 7/2000 | Callahan et al. |
| 6,110,202 A | 8/2000 | Barraquer et al. |
| 6,117,171 A | 9/2000 | Skottun |
| 6,120,538 A | 9/2000 | Rizzo, III et al. |
| 6,197,059 B1 | 3/2001 | Cumming |
| 6,200,342 B1 | 3/2001 | Tassignon |
| 6,217,612 B1 | 4/2001 | Woods |
| 6,299,641 B1 | 10/2001 | Woods |
| 6,443,985 B1 | 9/2002 | Woods |
| 6,797,004 B1 | 9/2004 | Brady et al. |
| 6,930,838 B2 | 8/2005 | Schachar |
| 7,097,660 B2 | 8/2006 | Portney |
| 7,125,422 B2 | 10/2006 | Woods et al. |
| 7,150,759 B2 | 12/2006 | Paul et al. |
| 7,179,292 B2 | 2/2007 | Worst et al. |
| 7,220,279 B2 | 5/2007 | Nun |
| 7,503,938 B2 | 3/2009 | Phillips |
| 7,713,299 B2 | 5/2010 | Brady et al. |
| 7,815,678 B2 | 10/2010 | Ben Nun |
| 2003/0004569 A1 | 1/2003 | Haefliger |
| 2004/0082993 A1 | 4/2004 | Woods |
| 2004/0082995 A1 | 4/2004 | Woods |
| 2004/0111153 A1 | 6/2004 | Woods et al. |
| 2005/0018504 A1 | 1/2005 | Marinelli et al. |
| 2005/0021139 A1 | 1/2005 | Shadduck |
| 2005/0131535 A1 | 6/2005 | Woods |
| 2006/0238702 A1 | 10/2006 | Glick et al. |
| 2007/0078515 A1 | 4/2007 | Brady |
| 2007/0100444 A1 | 5/2007 | Brady et al. |
| 2007/0106381 A1 | 5/2007 | Blake |
| 2007/0129798 A1 | 6/2007 | Chawdhary |
| 2007/0135915 A1 | 6/2007 | Klima |
| 2007/0213817 A1 | 9/2007 | Esch et al. |
| 2007/0260309 A1 | 11/2007 | Richardson |
| 2008/0161914 A1 | 7/2008 | Brady et al. |
| 2009/0012609 A1 | 1/2009 | Geraghty et al. |
| 2009/0163602 A1 | 6/2009 | Hu et al. |
| 2010/0094415 A1 | 4/2010 | Bumbalough |

FOREIGN PATENT DOCUMENTS

| | | |
|---|---|---|
| EP | 766540 B1 | 8/1999 |
| EP | 2219065 A1 | 8/2010 |
| JP | 2126847 A | 5/1990 |
| WO | WO0119288 A1 | 3/2001 |
| WO | WO0219949 A2 | 3/2002 |
| WO | WO2005115278 A1 | 12/2005 |
| WO | 2008083283 A2 | 7/2008 |

OTHER PUBLICATIONS

English translation of WO93/05733A1.
U.S. Appl. No. 09/656,661, filed Sep. 7, 2000.
Thornton S., "Accommodation in Pseudophakia," 1991, pp. 159-162.
U.S. Appl. No. 09/721,072, filed Nov. 22, 2000.

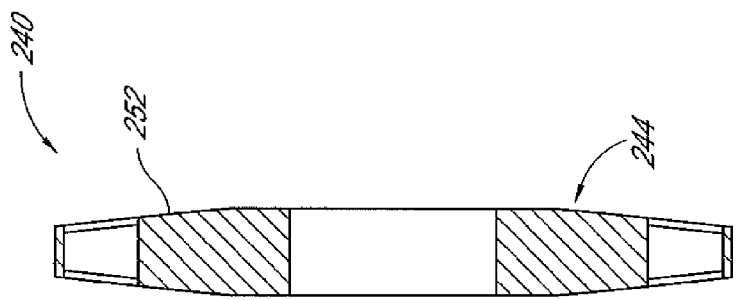
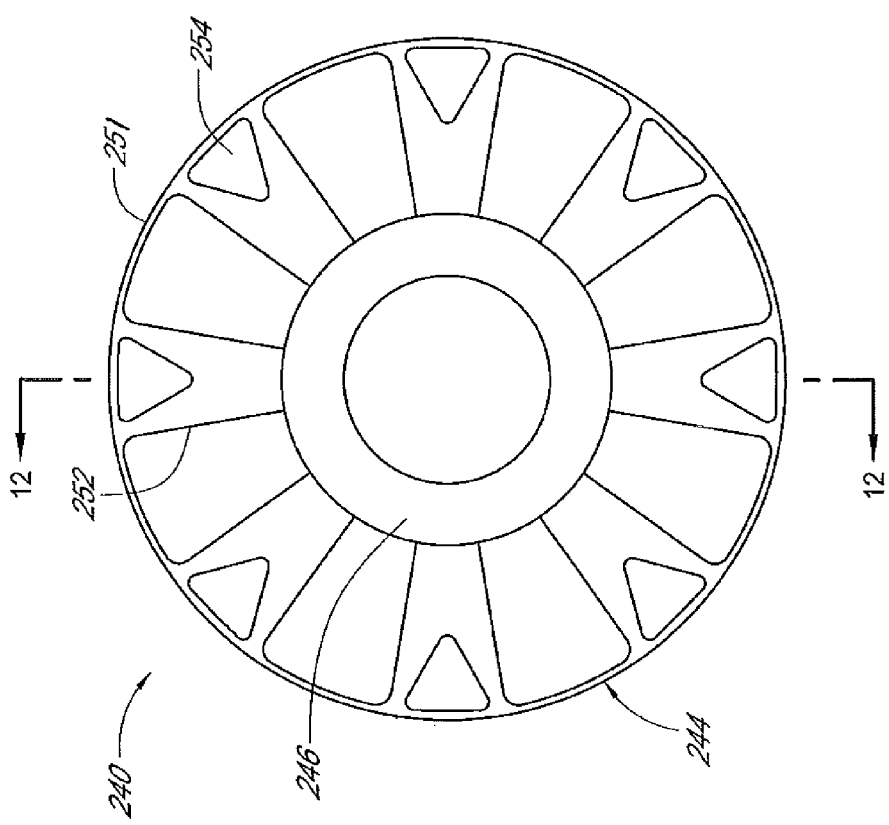

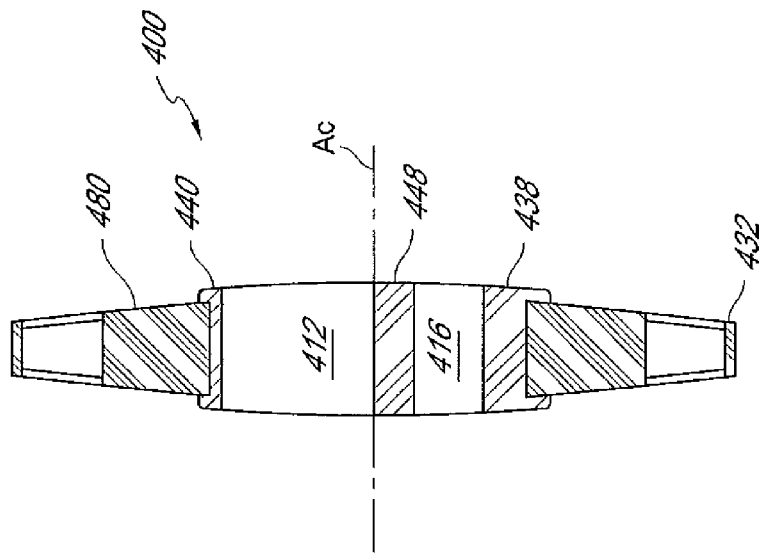
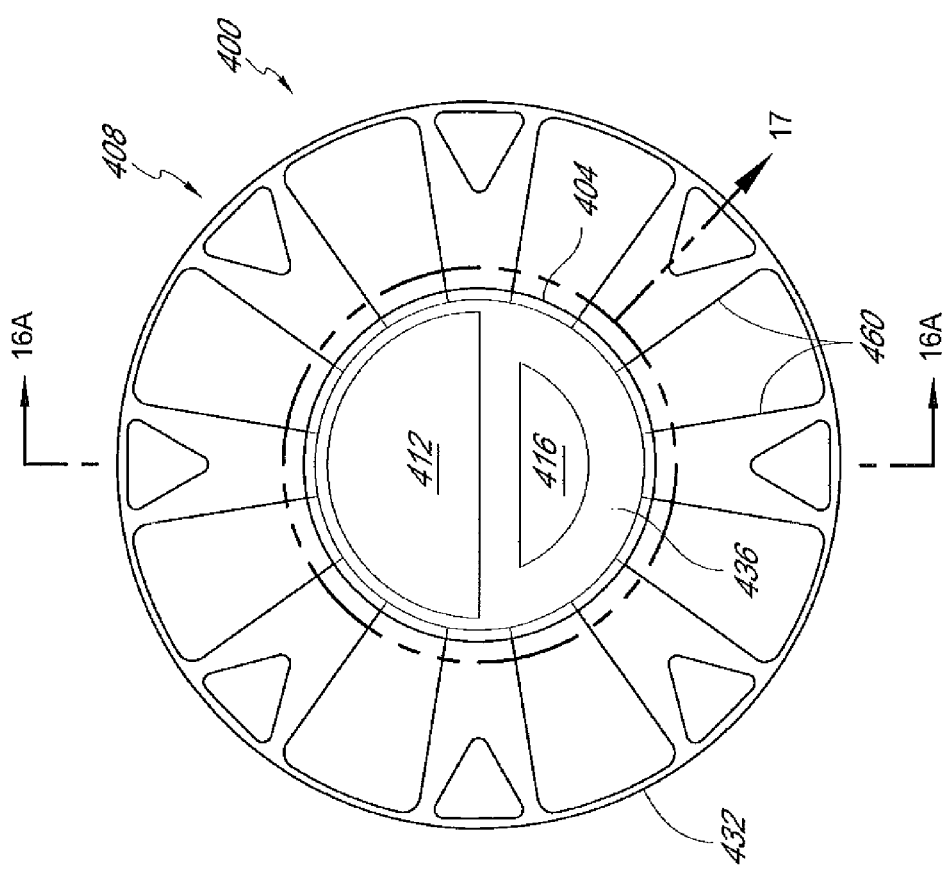
FIG. 16A
FIG. 16

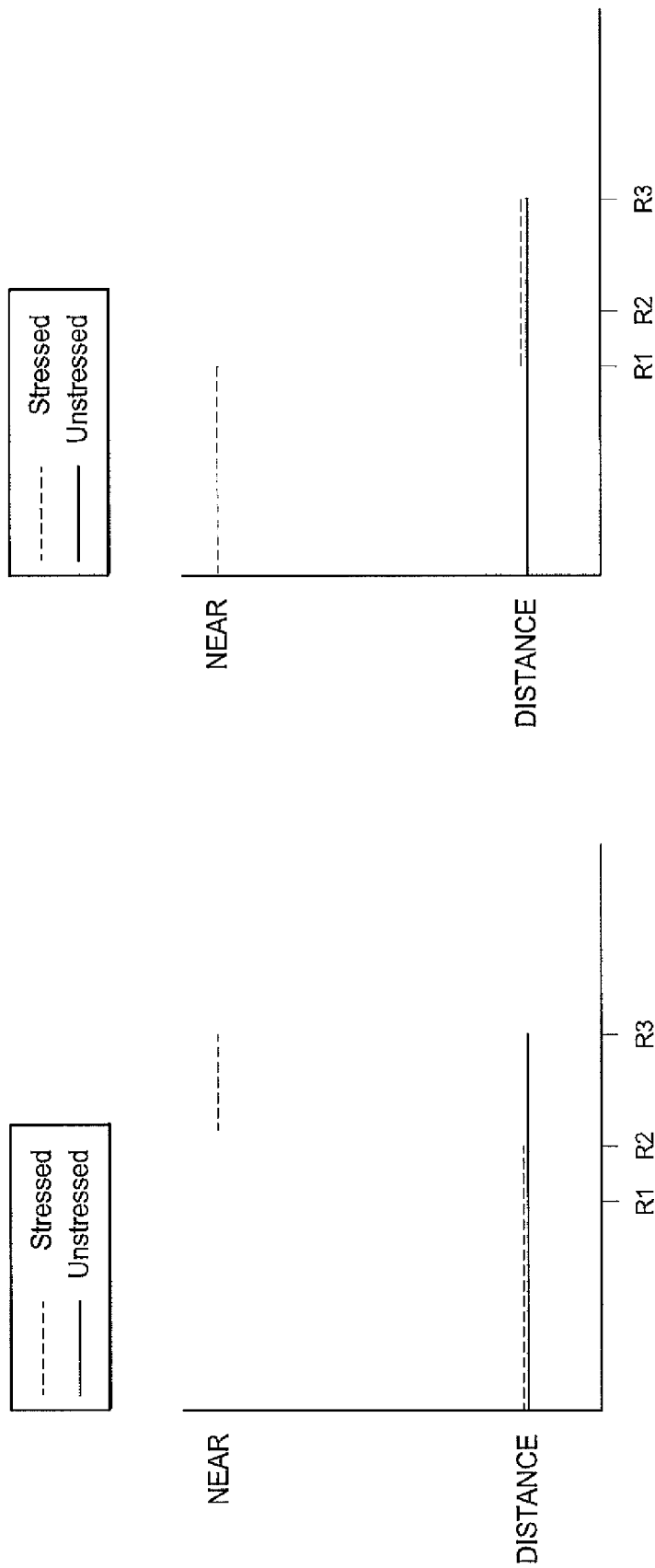

INTRAOCULAR LENS WITH SHAPE CHANGING CAPABILITY TO PROVIDE ENHANCED ACCOMODATION AND VISUAL ACUITY

BACKGROUND OF THE INVENTION

1. Field of the Invention

The present invention is directed to intraocular lenses, and more particularly to accommodating intraocular lenses having more than one focus, an extended depth of focus, or enhanced performance through asymmetric transfer of ocular forces in the lenses.

2. Description of the Related Art

A human eye can suffer diseases that impair a patient's vision. For instance, a cataract may increase the opacity of the lens, causing blindness. To restore the patient's vision, the diseased or damaged lens may be surgically removed and replaced with an artificial lens, known as an intraocular lens, or IOL. An IOL may also be used for presbyopic lens exchange or other elective ocular surgical procedures.

Monofocal IOLs have a single focal length, or, equivalently, a single power. Unlike the eye's natural lens, which can adjust its focal length within a particular range in a process known as accommodation, these single focal length IOLs cannot accommodate and thus provide clear vision over a limited range of distances. As a result, distant objects may appear in focus, while objects at a normal reading distance from the eye may appear blurred.

Vision over a broader range of distances can be obtained either through the use of a multifocal lens, which provides different foci configured to produce overlapping focused images for different object distances, or a lens configured to provide an extended depth of focus or depth of field, through for example, an aspheric surface. While such lenses can improve the overall vision range, there may also be an associated reduction in visual acuity or overall visual quality, as well as dysphotopsias.

Another approach is to use an accommodating IOL, which can adjust its axial position, shape, and/or thickness to effect an optical power change within a particular range, similar to the eye's natural lens. As a result, the patient can clearly focus on objects in a range of distances from the eye, rather than at a single distance, or a limited number of set distances. This ability to accommodate is of tremendous benefit for the patient, and more closely approximates the patient's natural vision than a single focal length IOL. One of the challenges in accommodating IOLs is providing a sufficient range of accommodation with the limited amount of ocular force available from the ciliary muscle. Additional challenges with IOLs, including accommodating IOLs include optical aberrations, such as astigmatism, coma, spherical aberration, for example.

SUMMARY OF THE INVENTION

Embodiments of the present invention are directed to devices and methods for providing accommodative vision. In one aspect, an intraocular lens is provided that comprises an adjustable optic adapted to focus light on the retina when disposed in the eye and a haptic or mounting structure that is operably coupled to the optic. The intraocular lens is asymmetric in at least one aspect that concentrates deformation of the optic to enhance the accommodative effect or for other optical benefits, as discussed below.

In one embodiment the optic has a first zone that has a distance vision power and a second zone that has a range of powers greater than the distance vision power. The range of powers of the second zone includes a near vision power. The first zone is intersected by a central optical axis and the second zone is off-set from the first zone. The haptic includes an outer annular member and an inner annular member. The inner annular member can be disposed inside at least the second zone of the optic. The haptic also includes a plurality of arms extending between the inner and outer annular members. The intraocular lens is adapted to respond to ocular forces to adjust the power of the second zone toward the near vision power.

In certain embodiments, the range of powers in the second zone refers to the instantaneous maximum power of the second zone as it is being deformed through its range of accommodation. In other embodiments, a range of powers is provided at each stage of accommodation, for example including an extended depth of focus configuration at least in the fully accommodated state.

In another embodiment, an intraocular lens is provided that includes an adjustable optic and a haptic. The adjustable optic has an optical area adapted to focus light on the retina when the intraocular lens is disposed in the eye. The haptic includes a plurality of arms connected at their distal ends by a ring disposed adjacent an outer periphery of the intraocular lens. Some of the arms are connected at their proximal end by a ring portion subtending an arc of about 180 degrees or less between first and second ends. The ring portion can comprise a plurality of ring segments extending between adjacent arms. The first and second ends of the ring portion are connected by a transverse member extending across the optical area. The ring portion and transverse member of the haptic are disposed inside the adjustable optic. The intraocular lens has a first zone and a second zone, the second zone being disposed between the transverse member and the ring portion. The transverse member is disposed between the second zone and the first zone. The intraocular lens has an unstressed configuration in which first and second zones provide a first optical power for distance vision and a stressed configuration in response to ocular forces in which the second zone provides a second optical power that is greater than the first optical power.

In another embodiment, an intraocular lens is provided that includes an optic and a haptic. The optic has a fixed power region and an add power region. The haptic includes an inner portion having a stiff region disposed inside the fixed power region and a force transfer portion disposed inside the add power region. The haptic also includes a plurality of arms extending radially away from the force transfer portion toward an outer periphery of the intraocular lens. The intraocular lens is adapted to respond to ocular forces to alter the add power region and increase the power of the add power region.

In another embodiment, an intraocular lens is provided that includes an optic and a haptic. The optic comprises a fixed power region and an add power region that includes a gel. The haptic includes an inner portion, a force transfer portion, and a plurality of arms. The inner portion is disposed inside the fixed power region. The force transfer portion is disposed inside the add power region. At least some of the arms extend radially away from the force transfer portion toward an outer periphery of the intraocular lens. The intraocular lens is adapted to respond to ocular forces to preferentially apply a greater amount of force to the add power region to increase the power of the add power region.

In various embodiments, the haptic comprises a transparent portion protruding into the adjustable optic. The intraocular lens has a disaccommodative configuration in which an adjustable zone has a base optical power and an accommodative configuration in which the adjustable zone has an add optical power that is at least about 1 Diopter greater than the base optical power, preferably at least about 2 Diopters greater than the base optical power, and even more preferably at least 3 Diopters, or even 4 Diopters, greater than the base optical power. The adjustable zone can be bordered by an annular zone having different optical powers when the adjustable intraocular lens is in the accommodative configuration and/or in the disaccommodative configuration.

As used herein "base optical power" or "base power" means power (in Diopters) of an IOL or other ophthalmic lens or lens system that is required to provide distant vision at the retina of a subject eye. As used herein "add optical power" or "add power" means a difference in power (in Diopters) between the power required to provide distant vision and the power of the lens portion having the add optical power. When the add optical power is a positive quantity, it is the difference in power between power required to provide distant vision and the power required to focus light from an object at some finite distance from the eye. Alternatively, the add optical power may be a negative quantity.

In another aspect of the present invention, a method of providing accommodative vision to a subject comprises providing an intraocular lens according to an embodiment of the invention that includes an optic having an off-set add power region and/or asymmetric force transfer capability. The method also comprises placing the intraocular lens into the eye of a subject in a disaccommodated configuration in which the off-set add power region has a base optical power or in which an optic of an intraocular lens configured for asymmetric loading is unstressed. The intraocular lens is adjustable to an accommodated configuration in which the off-set add power region has an add optical power that is at least 1 to 4 Diopters greater than the base optical power. The off-set add power region and a portion of the optic spaced apart from the add power region may simultaneously have different optical powers when the intraocular lens is in the accommodated configuration and/or when the optic is in the disaccommodative configuration. In another method, a further aspect comprises asymmetrically loading an optic to compensate for anatomical asymmetry. Anatomical asymmetry may include optical aberrations due to asymmetry in the eye system and/or non-uniform loading due to damage to the ocular muscles or connective tissues.

Alternatively, the intraocular lens may be placed into the eye in an accommodated configuration in which the off-set add power zone has the add optical power, wherein the intraocular lens is adjusted to a disaccommodated configuration in which the off-set add power zone has a base optical power that is suitable for providing intermediate and/or distant vision. In any event, when the intraocular lens is in the accommodated configuration, the off-set add power zone and/or spaced apart zone is suitable for providing vision for objects that are relatively close to the subject (e.g., 12 to 24 inches from the subject) or objects at intermediate distances (e.g., 2 to 5 feet from the subject). When the intraocular lens is in the disaccommodated configuration, the off-set add power zone and/or spaced apart zone is suitable for providing vision for objects that are distant (e.g., greater than 20 feet from the subject) and/or objects at intermediate distances.

In another embodiment, an intraocular lens is provided that includes an optic adapted to be deformed by a haptic when subjected to a compressive ocular force. The haptic is adapted to apply, in response to a uniform annular compressive ocular force, a first compressive force to a first portion of the optic and a second compressive force to a second portion of the optic. The second ocular force is different from the first ocular force. The first and second portions of the optic change power when subjected to the compressive ocular force. The first portion of the optic changes power by an amount greater than the second portion. The haptic may include a plurality of arms connected at their distal ends by a ring disposed adjacent an outer periphery of the intraocular lens, some of the arms being connected at their proximal end by a ring portion subtending an arc of about 180 degrees or less between first and second ends, the first and second ends being connected by a transverse member extending across the optical area, the ring portion and transverse member of the haptic being disposed inside the adjustable optic; wherein the intraocular lens has a first zone and a second zone, the second zone being disposed between the transverse member and the ring portion, the transverse member being disposed between the second zone and the first zone; wherein the intraocular lens has an unstressed configuration in which first and second zones provide a first optical power for distance vision and a stressed configuration in response to ocular forces in which the second zone provides a second optical power that is greater than the first optical power.

In another embodiment, an intraocular lens is provided that includes an optic and a haptic. The optic has a non-uniform geometry and is adapted to be deformed when subject to a compressive ocular force. The haptic is adapted to apply a compressive force along a first axis of the optic in response to the compressive ocular force and a compressive force along a second axis of the optic in response to the compressive ocular force. The compressive forces cause a change in curvature along the first axis that is greater than a change of curvature along the second axis. In another embodiment, rather than deform along a specific axis in response to an ocular force, the optic may vault anteriorly or posteriorly along a particular axis in response to an ocular force.

BRIEF DESCRIPTION OF THE DRAWINGS

Embodiments of the present invention may be better understood from the following detailed description when read in conjunction with the accompanying drawings. Such embodiments, which are for illustrative purposes only, depict novel and non-obvious aspects of the invention. The drawings include the following figures.

FIG. 11 is a front view of the haptic only from the intraocular lens shown in FIG. 9.

FIG. 12 is a cross-sectional view through the section 12-12 of FIG. 11.

FIG. 16 is a front view of an intraocular lens according to a fourth embodiment.

FIG. 16A is a cross-sectional view of the intraocular lens of FIG. 16 taken at 16A-16A.

FIG. 19A is a plot illustrating the optical power of one embodiment of an intraocular lens shown in FIG. 16 as a function of transverse location and accommodative state.

FIG. 19B is a plot illustrating the optical power of another embodiment of an intraocular lens similar to that shown in FIG. 16 as a function of transverse location and accommodative state.

DETAILED DESCRIPTION OF THE PREFERRED EMBODIMENT

In a healthy human eye, the natural lens is housed in a structure known as the capsular bag. During natural accommodation, the capsular bag is driven by a ciliary muscle and zonular fibers (also known as zonules) in the eye, which can pull on the capsular bag to change its shape. The change in shape of the capsular bag generally deforms the natural lens in order to change its power and/or the location of the lens, so that the eye can focus on objects at varying distances away from the eye in a process known as accommodation.

I. Intraocular Lenses Adapted to Accommodate by Changing the Shape of an Optic Embodiments described herein are directed to intraocular lenses that advantageously use ocular forces, such as those produced by the ciliary muscle, zonules, and/or capsular bag, to change the shape of the lens optic. Such an accommodating lens may produce improved vision over a lens with a fixed power and location that does not accommodate. As used herein the term "ocular force" is a broad term that includes a force that is sufficient to provide accommodation in the eye of a healthy human subject.

Figure 1:
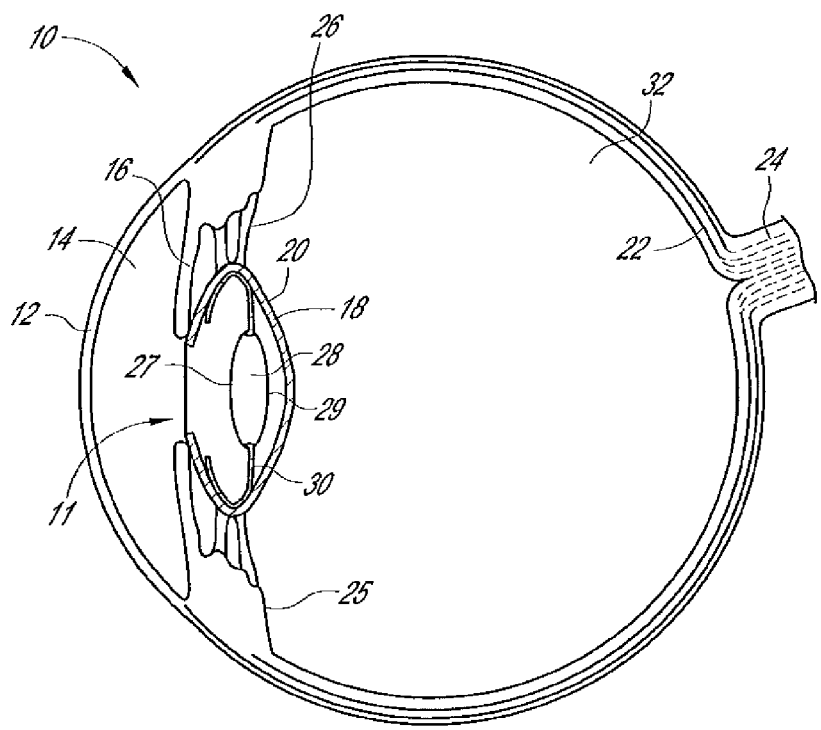
FIG. 1 is a plan drawing of a human eye having an implanted intraocular lens in an accommodative or "near" state.

FIG. 1 shows a human eye 10, after an accommodating intraocular lens 11, according to an embodiment of this application, has been implanted. Prior to surgery, the natural lens occupies essentially the entire interior of the capsular bag 18. After surgery, the capsular bag 18 may house the intraocular lens 11. Alternatively, the intraocular lens 11 may be configured to directly engage the zonules or ciliary muscle.

Light enters the eye 10 from the left in FIG. 1 and passes through the cornea 12, the anterior chamber 14, the pupil (defined by the inner edge of the iris 16), and impinges on the intraocular lens 11. After passing through the intraocular lens 11, light exits the posterior wall 20 of the capsular bag 18, passes through the vitreous body 32, and strikes the retina 22, which detects the light and converts it to a signal transmitted through the optic nerve 24 to the brain.

A well-corrected eye focuses an image at the retina 22. If the intraocular lens 11 has too much or too little power, the focused image shifts axially along the optical axis off of the retina, toward or away from the lens 11. Note that the total power of the eye (e.g., including the combined power of cornea 12 and the intraocular lens 11) required to focus on a close or near object is more than the power required to focus on a distant or far object. The difference between the "near power" and "far power" is known typically as the range of accommodation or the add power. A typical range of accommodation or add power is about 2 to 4 diopters, but may be significantly larger for younger human subjects.

The intraocular lens 11 may be designed so that its relaxed or natural state is the "far" or "distant" condition (sometimes referred to as a "disaccommodative biased" intraocular lens), the "near" condition (an "accommodative biased" intraocular lens), or some condition in between the two. As used herein, the terms "natural state", "natural configuration", "relaxed state", and "relaxed condition" can refer to a condition of an intraocular lens in which no or minimal external forces (e.g., ocular forces from the ciliary muscle, zonules, or capsular bag) are acting upon the intraocular lens 11 or the optic 48 of an intraocular lens 40 (discussed below).

The capsular bag 18 is acted upon by the ciliary muscle 25 and the zonules 26, which distort the capsular bag 18 by stretching it radially in a relatively thick band about its equator. Experimentally, it is found that the ciliary muscle 25 and/or the zonules 26 typically exert a total force of up to about 10 grams of force, which is generally distributed uniformly around an equatorial region of the capsular bag 18. In some patients, non-uniform forces may be applied to the capsular bag 18, for example, due to damage of the zonules, which can cause astigmatism or other optical aberrations. As will be discussed in greater detail below, some embodiments disclosed herein are adapted to compensate for such non-uniformity.

Although the range of ocular force may vary from patient to patient, the range of accommodation for each subject is generally limited by the total ocular force available. Therefore, it is generally preferred that the intraocular lens 11 be configured to vary its power over the full range of accommodation in response to this limited range of ocular forces (e.g., to provide at least 2 Diopters, preferably 3 Diopters or more preferably 4 Diopters of accommodative power). In other words, it is desirable to have a relatively large change in power for a relatively small driving force. Alternatively, the effective range of accommodation may be increased by incorporating a lens having a multifocal or extended depth-offocus configuration. As discussed in connection with FIGS. 16-22 below, focusing the add power to a region of the intraocular lens can enhance the add power for that region and for the lens. As discussed in connection with FIGS. 23-24, asymmetric force transfer to an optic of an intraocular lens can counteract optical aberrations due to non-uniform characteristics of the eye, or alternatively may enhance such aberrations to achieve an extended depth of focus.

The intraocular lens 11 generally has an optic 28 made of a transparent, deformable and/or elastic material and a haptic 30 configured to hold the optic 28 in place and to mechanically transfers forces from the eye (e.g., from the capsular bag 18 or ciliary muscle 25) to the optic 28. The haptic 30 may have an engagement member with a central recess that is sized to receive the peripheral edge of the optic 28.

When the eye 10 is focused on a relatively close object, as shown in FIG. 1, the ciliary muscle 25 is compressed, which causes the zonules 26 to relax and allow the equatorial region of the capsular bag 18 to contract. The capsular bag 18 in this state is thicker at its center and has more steeply curved sides. As a result, the power of the lens is relatively high (e.g., the radii of curvature of one or both of the lens surfaces can decrease, and/or the lens can become thicker, and/or the lens can move axially), focusing the image of the relatively close object at the retina 22. Note that if the lens could not accommodate, the focused image of the relatively close object would, for an emmetropic eye, be located behind the retina, and would appear blurred. Also, if the eye has aberrations such as astigmatism, uniform power in all diameters or segments of the lens would not produce satisfactory vision. For some axes or segments, light would focus at the retina and for others light would focus behind or in front of the retina.

Figure 2:
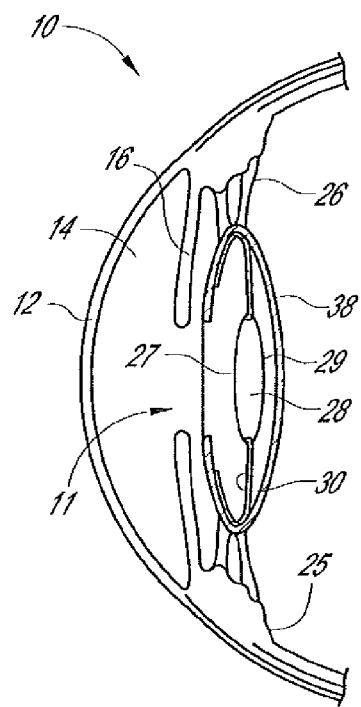
FIG. 2 is a plan drawing of the human eye of FIG. 1 in a disaccommodative or "far" state.
Figure 3:
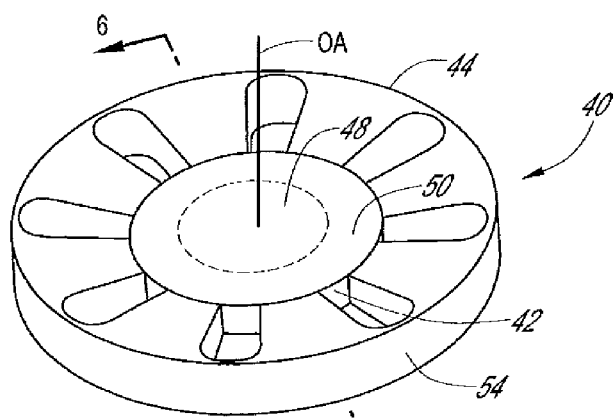
FIG. 3 is an isometric view of an intraocular lens according to a first embodiment showing an optic operably coupled to a haptic.
Figure 4:
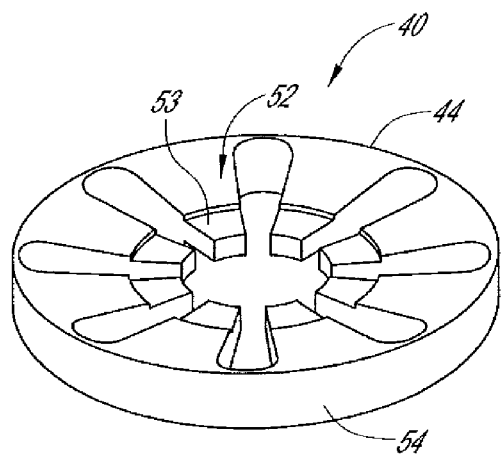
FIG. 4 is an isometric view of the haptic only from the intraocular lens shown in FIG. 3.
Figure 5:
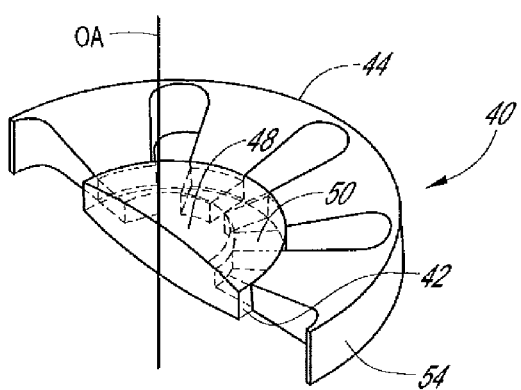
FIG. 5 is a cross-sectional isometric view of the intraocular lens of FIG. 3 showing a haptic segment operably coupled to an optic segment.

FIG. 2 shows a portion of the eye 10 focused on a relatively distant object. To focus on the distant object, the zonules 26 are retracted and the shape of the capsular bag 38 is thinner at its center and has less steeply curved sides. This reduces the lens power by flattening (i.e., lengthening radii of curvature and/or thinning) the lens and/or moving the lens axially, thus placing the image of the relatively distant object at the retina (not shown).

For both the "near" case of FIG. 1 and the "far" case of FIG. 2, the accommodating intraocular lens deforms and changes shape in response to the ciliary muscle 25 and/or to the distortion of the capsular bag 18. For the "near" object, the haptic 30 compresses the optic 28 at its edge, increasing the thickness of the optic 28 at its center and more steeply curving its anterior face 27 and/or its posterior face 29. As a result, the lens power increases. For the "far" object, the haptic 30 expands, reducing the compressive force on the edge of the optic 28, and thereby decreasing the thickness of the optic 28 at its center and less steeply curving (e.g., lengthening one or both radius of curvature) its anterior face 27 and/or its posterior face 29. As a result, the lens power decreases.

The specific degrees of change in curvature of the anterior and posterior faces 27, 29 depend on the nominal curvatures. Although the optic 28 is drawn as bi-convex, it may be plano-convex, meniscus or other lens shapes in other embodiments. In all of these cases, the optic 28 is compressed or expanded by forces from the haptic to the edge and/or faces of the optic 28. In addition, there may be some axial movement of the optic 28. In some embodiments, the haptic 30 is configured to transfer the generally symmetric radial forces symmetrically to the optic 28 to deform the optic 28 in a spherically symmetric way.

In alternate embodiments discussed in connection with FIGS. 16-18, 20-24, the haptic 30 is configured non-uniformly (e.g., having different material properties, thickness, dimensions, spacing, angles or curvatures), to allow for non-uniform transfer of forces by the haptic 30 to the optic 28. The non-uniform force transfer can enhance accommodative deformation in a sub-region to increase the add power in that sub-region as discussed in connection with FIG. 16-22. Also, for example, as discussed in connection with FIGS. 23-24, non-uniform force transfer could be used to compensate for astigmatism, coma or other asymmetric aberrations of the eye/lens system, including asymmetric natural forces in the ciliary process (e.g. if certain zonules are broken). The optic 28 may optionally have one or more diffractive, multifocal, and/or aspheric elements or surfaces, which can be provided in the relaxed state or induced by forces transferred by the haptic 30.

A. Intraocular Lenses with Cantilevered Haptic Arms

Referring to FIGS. 3-7B, in certain embodiments, an intraocular lens 40 comprises an adjustable optic 42 and a haptic 44. The optic 42 has a clear aperture 43 that includes an anterior surface 45 and a posterior surface 46. The clear aperture includes a central zone 48 disposed about an optical axis OA and a surrounding or annular zone 50 surrounding the central zone 48.

The haptic 44 may comprise a plurality of arms 52 that protrude into the adjustable optic 42 and into the clear aperture 43. As discussed in connection with the embodiments below, a modified haptic 44 is provided that is not uniform, for example in which some of the arms 52 have greater capacity to transfer forces to an optic and some with less force transfer capacity. In order to provide a large clear aperture, the haptic 44 and arms 52 includes transparent or refractive index matched (to the optic) portions 53 that protrude into the adjustable optic 42 and into the clear aperture 43. The haptic 44 and arms 52 generally protrude into the annular zone 50 but may also partially protrude into the central zone 48. The haptic 44 and arms 52 are configured to deform the central zone 48 in response to an ocular force from the ciliary muscle and/or capsular bag, thereby changing the power of the central zone 48 by at least 1 Diopter, preferably by at least 2 Diopters or at least 4 Diopters. By contrast the annular zone 50 may not change shape in response to an ocular force or changes shape by an amount that produces less accommodative power change than the power change of the central zone 48 (e.g., changes power by less than 1 Diopter in response to an ocular force, less than 0.5 Diopters in response to an ocular force, or less than 0.25 Diopters in response to an ocular force).

The transparent portion 53 preferably has a transmissivity of at least about 80%, more preferably of at least 90% or even 95%. In some embodiments, the haptic 44 is made of a material that has a refractive index that is substantially equal to the refractive index of the optic 42, thus reducing or eliminating glare and aberration problems that could be introduced by a mismatch in refractive indices.

As used herein, the term "clear aperture" means the opening of a lens or optic that restricts the extent of a bundle of light rays from a distant source that can imaged or focused by the lens or optic. The clear aperture can be circular and specified by its diameter. Thus, the clear aperture represents the full extent of the lens or optic usable for forming the conjugate image of an object or for focusing light from a distant point source to a single focus or to a plurality of predetermined foci, in the case of a multifocal optic or lens. It will be appreciated that the term clear aperture does not limit the transmittance of the lens or optic to be at or near 100%, but also includes lenses or optics having a lower transmittance at particular wavelengths or bands of wavelengths at or near the visible range of the electromagnetic radiation spectrum. In some embodiments, the clear aperture has the same or substantially the same diameter as the optic 42. Alternatively, the diameter of the clear aperture may be smaller than the diameter of the optic 42, for example, due to the presence of a glare or PCO reducing structure disposed about a peripheral region of the optic 42.

Figure 6:
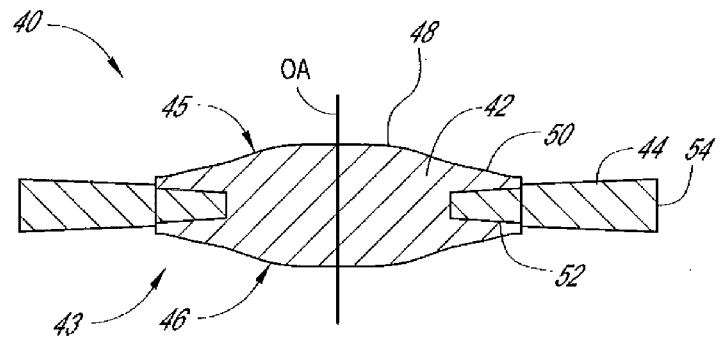
FIG. 6 is a cross-sectional view through the section 6-6 of FIG. 3 showing a portion of a haptic protruding into an optic and the intraocular lens in a disaccommodative state.
Figure 7A:
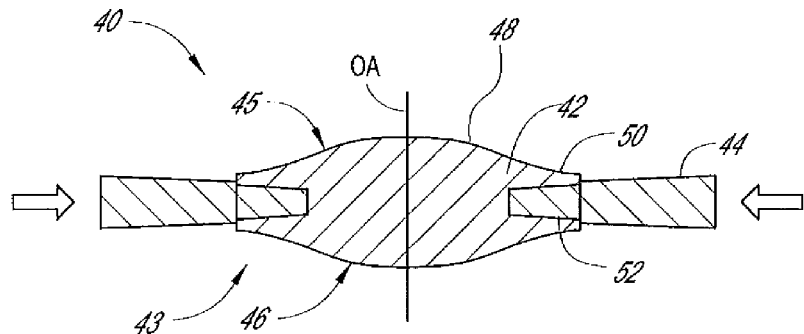
FIG. 7A is a cross-sectional view of the intraocular lens shown in FIG. 6 in an accommodative state.

The intraocular lens 40 and the optic 42 may be adjusted between an accommodative state and a disaccommodative state. For example, referring to FIG. 6, the optic 42 has a disaccommodative configuration or state in which the central zone 48 has a base optical power suitable for distant vision. Referring to FIG. 7A, the intraocular lens 40 has an accommodative configuration or state in which the central zone 48 has an add optical power suitable for near or intermediate vision. The base optical power is generally selected to provide a subject with distant vision (e.g., for objects at distances greater than 10 feet from the subject), while the add optical power of central zone 48 may be exploited to provide a subject with better vision for near objects (e.g., for objects at distances between about 12 to 24 inches from the subject) and/or intermediate distances (e.g., for objects at distances between 2 to 10 feet from the subject). Accordingly, the add power is preferably at least about 1 Diopter greater than the base optical power, more preferably at least 2 Diopters greater than the base optical power, and even more preferably at least 3 Diopters or 4 Diopters greater than the base optical power. In the illustrated embodiment, the add optical power is produced by the thickening of the lens which leads to a decreased radius of curvature of the anterior and posterior surfaces 45, 46, as illustrated by comparing FIG. 7A to FIG. 6. In some embodiments, the optical add power may be supplemented by accommodative movement of the optic 40 in the anterior direction (e.g., away from the retina of the eye). While the add optical power will generally comprise a positive change in the accommodative power, the add optical power may alternatively be a negative add power.

Figure 7B:
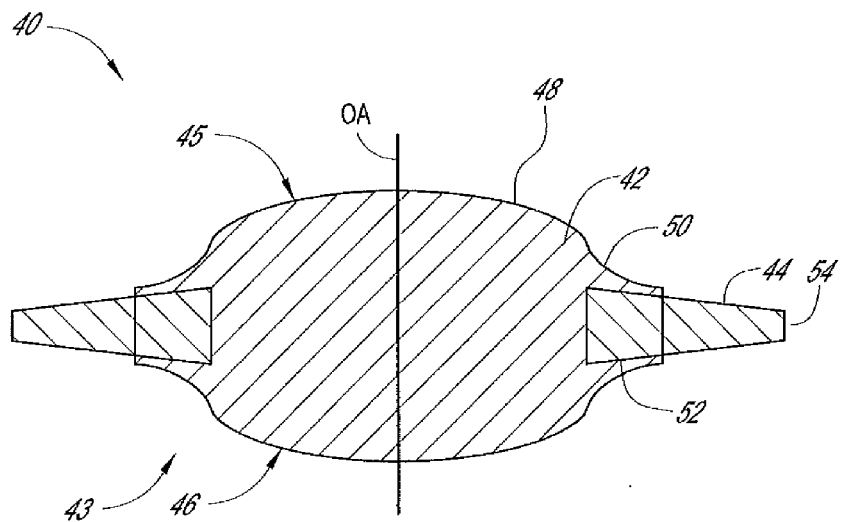
FIG. 7B is a cross-sectional view of an intraocular lens showing a portion of a haptic protruding into an optic, the haptic having a larger circumference or perimeter toward the central zone of the optic and a smaller circumference or perimeter at the edge of the optic.

In certain embodiments, the surrounding zone 50 also has a base optic power when the intraocular lens 40 is in a disaccommodative state and an add optical power when the intraocular lens 40 is in an accommodative configuration. The add optical power of the surrounding zone 50 may be equivalent to the add optical power of the central zone 48. Alternatively, the add optical power of the surrounding zone 50 may be greater than or less than the add optical power of the central zone 48. This difference in the add power between the central and surrounding zones 48, 50 may be the result of differences in how forces on the haptic 44 are transferred to the zones 48, 50, as well as the shape of the haptics in the various zones. By way of nonlimiting example, a haptic with a larger axial thickness at the edge of optic which then tapers as it protrudes into the optic may have a greater effect on the surrounding zone as opposed to the central zone. Conversely a haptic with a small axial thickness at the edge of the optic and a larger axial thickness toward the central zone may have a greater effect on the central zone as opposed to the surrounding zone as shown in FIG. 7B.

Other modified intraocular lens embodiments discussed below provide add power in a region located only on one side of a diameter of an optic or in a particular portion or along a particular axis of the optic. The ocular forces are concentrated into a particular region to enhance add optical power in that region.

In addition to providing accommodative power, the central and surrounding zones 48, 50 may combine, in certain preferred embodiments, to provide a multifocal lens when the intraocular lens is in the accommodative state, the disaccommodative states, and/or at intermediate states therebetween. Thus, for any given state or configuration of the central and annular zones 48, 50, the intraocular lens 40 may be configured to generally provide an extended depth of focus or multiple foci that allows resolution of objects at varying distances (e.g., simultaneously providing near and intermediate vision, or simultaneously providing intermediate and distant vision).

The multifocality of the intraocular lens 40 (e.g., the differences in optical power of the central and surrounding zones 48, 50) may be produced by a radius of curvature between the anterior and/or posterior surfaces 45, 46 of the central zone 48 and the surrounding zone 50. For example, referring to FIGS. 6 and 7A, the radius of curvature of the anterior and posterior surfaces 45, 46 in the region of central zone 48 is less than the radius of curvature of those surfaces in the region of the surrounding zone 50, both in the accommodative state (FIG. 7A) and disaccommodative state (FIG. 6). It will be appreciated that the differences in the radiuses of curvature in the central and annular zones 48, 50 have been exaggerated for illustrative purposes. In some embodiments, the larger radius of curvature in the surrounding zone 50 is selected to provide distant vision, while the smaller radius of curvature of the central zone 48 is selected to provide a larger optical power suitable for intermediate vision and/or near vision. In some embodiments, the difference in optical power of the two zones 48, 50 is at least partially provided by a diffractive grating or phase plate that is placed on one or both surfaces of the central zone 48 and/or the surrounding zone 50.

In the illustrated embodiment, the central zone 48 has a greater optical power than the surrounding zone 50. Alternatively, the central zone 48 may have the same or less optical power than the surrounding zone 50 when the intraocular lens 40 is in the accommodative configuration, the disaccommodative configuration, or in some state between the accommodative and disaccommodative configurations. In some embodiments, the zones 48, 50 are configured to have the same optical power (e.g., to be a monofocal lens having substantially a single focus) when the intraocular lens 40 is in either the accommodative state or disaccommodative state. Alternatively, the zones 48, 50 may be configured to have the same optical power at an intermediate state of the intraocular lens 40 and different optical powers when the intraocular lens 40 is in either the accommodative state or disaccommodative state.

The diameter of central and surrounding zones 48, 50 may selected to provide a predetermined mix of near, distant, and/or intermediate vision that varies as a function of lighting conditions (e.g., as a function of the amount of the optic 42 exposed as the iris of the varies in size). For example, diameter of the central zone 48 may be at least about 2-millimeters. Alternatively, the diameter of the central zone 48 may be greater than 3 millimeters or greater than 4 millimeters. In some embodiments, the outer diameter of the surrounding zone is greater than about 4 millimeters, preferably greater than or equal to 5 millimeters or greater than or equal to 6 millimeters. In certain embodiments, the optic 42 comprises one or more additional zones surrounding the zones 48, 50, for example, to further adjust the mixture of near, distant, and/or intermediate vision as a function of lighting conditions. In some embodiments, the optic 42 further comprises an intermediate or transition zone disposed between the central and surrounding zones 48, 50 that is configured, for example, to preclude discontinuities between the zones 48, 50 that could produce glare or other unwanted optic effects.

In some embodiments, the central zone 48 and/or the surrounding zone 50 has at least one surface 45, 46 that is aspheric and/or toric in shape and that may be configured to correct or enhance an aberration of the eye (e.g., astigmatism, spherical aberrations, coma, and the like). The aspheric or toric shape and associated correction may be present when the intraocular lens 40 is in the accommodative configuration, the disaccommodative configuration, or both the accommodative and disaccommodative configurations. For radially asymmetric configurations (e.g. toric), the toric shape may be oriented along any axis perpendicular to the optical axis, and preferably aligned to reduce the natural astigmatism in the eye. Alternatively the optic may be aligned to enhance or induce astigmatism, e.g., a vertical or horizontal astigmatism, in order to increase depth of focus. The central zone 48 and/or the surrounding zone 50 may comprises a diffractive grating or phase plate that is configured to increase or decrease the optical power of the one zone as compared to the remaining zone (which may also include a diffractive zone or grating having a different power). In some embodiments, the diffractive grating or phase plate may be configured to correct for or enhance a chromatic aberration.

The optic 42 and the haptic 44 may be integrally made of a single material with or without different characteristics. Alternatively, the optic 42 may be made of material from one family and the haptic 44 may be made of material from another family (e.g., one from an acrylic family member and the other from a silicone family member). One or both of the optic 42 and the haptic 44 may be made of a hydrophilic material. In some embodiments, the intraocular lens 40 is fabricated such that the optic 42 is stressed by the haptic 44 when the intraocular lens 40 is in a natural state in which there are no external forces acting on the intraocular lens 40. Examples of this type of pre-stressing of an optic are discussed in co-pending U.S. patent application Ser. No. 11/618,411, which is herein incorporated by reference. Other haptic configurations may be incorporated into embodiments of the present invention such as, for examples, those discussed in co-pending U.S. patent application Ser. No. 11/618,325, which is herein incorporated by reference.

The optic 42 may be made from a relatively soft material and configured so that at least a portion of the optic 42 distorts or changes shape readily under the limited deforming force initiated by the ciliary muscle and/or capsular bag and transmitted through the haptic 44. An exemplary material is a relatively soft silicone material, although other suitable materials may be used as well. The stiffness of the optic 42 may be less than 500 kPa, or preferably may be between 0.5 kPa and 500 kPa, or more preferably may be between 10 kPa and 200 kPa, or even more preferably may be between 10 kPa and 50 kPa or between 25 kPa and 50 kPa. In contrast with the optic 42, the haptic 44 may be made from a relatively stiff material, so that it can efficiently transmit the deforming forces from the capsular bag to the optic 42. As discussed below, various modified embodiments provide different force transfer capacity in different portions of a haptic, an optic, or both a haptic and an optic. An exemplary material is a relatively stiff silicone material, although other suitable materials may be used as well, such as acrylic, polystyrene, or clear polyurethanes. The haptic 44 may preferably be stiffer than the optic 42. The stiffness of the haptic 44 may be greater than 500 kPa, or preferably may be greater than 3000 kPa.

Various types of materials, haptic configurations, and/or optic configurations may be utilized to provide a predetermined amount of optic distortion or shape change in response to an ocular force, either to the optic 42 or to any other optic embodiment discussed or suggested herein. Examples of such materials and mechanisms for providing a desired amount of optic shape change or distortion due to ocular forces may be found in U.S. Pat. No. 7,125,422 and in US Patent Application Numbers 2004/0082993, 2004/0111153, and 2005/0131535), all of which are herein incorporated by reference in their entirety. As an example, the optic 42 may comprise an optic body and a liquid or gel material disposed within a void of the optic body. Such an optic structure may be configured to both provide a low optic stiffness and to maintain an overall optic shape that is suitable for vision.

Figure 8:
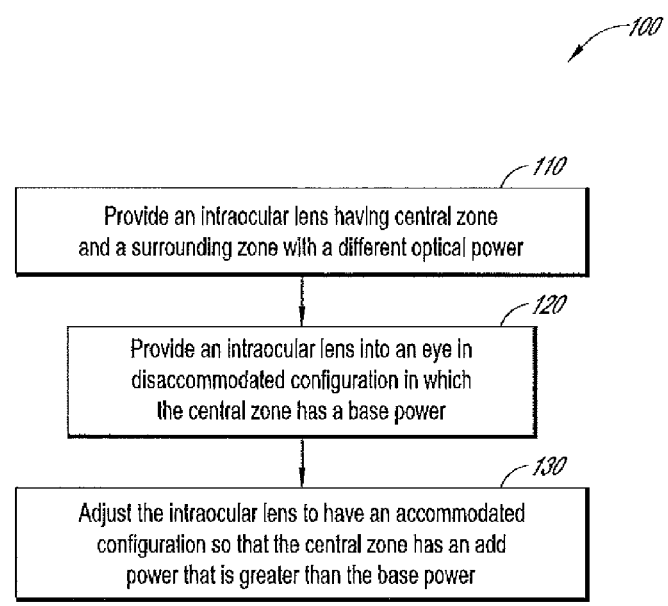
FIG. 8 is a block diagram of a method of implanting an intraocular lens and providing accommodative vision.

In certain embodiments, as seen in FIG. 8, a method 100 of implanting an intraocular lens and providing accommodative vision to a subject comprises an operational block 110 of providing the intraocular lens 40 having a central zone 48 and a surrounding zone 50. The method also comprises an operational block 120 of placing the intraocular lens 40 into the eye of a subject in a disaccommodated configuration in which the central zone has a base optical power. The method 100 further comprise an operational block 130 of adjusting or causing the intraocular lens to have an accommodated state within the eye in response to ciliary muscle contraction, wherein the central zone 48 has an add optical power that is at least 1 Diopter greater than the base optical power, preferably 2 Diopters greater than the base optical power, and even more preferably 3 to 4 Diopters greater than the base optical power. In some embodiments, the central zone 48 and the surrounding zone 50 simultaneously have different optical powers when the optic 42 is in the accommodated configuration and/or when the optic 42 is in the disaccommodative configuration. In some embodiments, the method is comprised of placing the intraocular lens 40 into the eye of a subject in an accommodated configuration wherein the central zone 48 has an add optical power that is at least 1 Diopter greater than the base optical power, preferably 2 Diopters greater than the base optical power, and even more preferably 3 to 4 Diopters greater than the base optical power.

The method 100 is generally used in conjunction with an intraocular lens having a disaccommodative bias. For example, the intraocular lens 42 may be configured to have a disaccommodative bias such that the surrounding zone 40 has an optical power that is selected to provide distant vision when the intraocular lens 40 is in a natural configuration in which there are no external forces on the haptic 44. Thus, when the intraocular lens 40 is placed into the eye 10, it has a relatively elongate shape in a direction that is perpendicular to the optical axis OA, as illustrated in FIG. 6.

In operational block 130, the intraocular lens is adjusted to have an accommodative configuration as an ocular force F (illustrated in FIG. 7A) radially pushes the haptic 44 toward the optical axis OA. This places the intraocular lens 40 in a stressed state or configuration so that the adjustable optic 42 deforms and/or thickens into a more oval shape that will increase the optical power of the central zone 48 and optionally increase the optical power of the surrounding zone 50. The ocular force F is typically within a range of at least about 1 gram to about 10 grams. Within the art, an understanding of the physiology of the eye is still developing. Thus, the range of ocular forces able to provide the above ranges of relative and/or absolute thickness change are anticipated as the physiology of the eye is better understood. Such ranges of ocular forces are also consistent with embodiments disclosed herein.

The intraocular lens 40 may be placed in the capsular bag 18 of the eye 10, 10, such that an outer periphery 54 of the haptic 44 is in contact with an equatorial region of the capsular bag 18. In such embodiments, a contraction of the ciliary muscle 25 causes the capsular bag 18 to produce the ocular force F, causing the intraocular lens 40 to be actuated into the accommodating configuration. Alternatively, the intraocular lens 40 may be configured for placement in another portion of the eye 10. For example, the intraocular lens 40 may be configured for placement such that the haptic 44 is in direct contact with the ciliary muscle 25 or even the zonules 26.

B. Accommodating Intraocular Lenses with Inner Arcuate Members

FIGS. 9-15 show various embodiments of intraocular lenses having haptics that include a member, which can be an arcuate member such as a ring or a plurality of ring segments, disposed inside of an optic. These embodiments can be arranged in a generally planar configuration as described in connection with FIGS. 9-12 or in a higher volume configuration, sometimes referred to herein as a bag-filling arrangement, as in FIGS. 13-15.

1. Generally Planar Configurations

Referring to FIGS. 9-12, an intraocular lens 240 comprising an adjustable optic 242 and a haptic 244 may be configured to have a disaccommodative bias when placed into the eye 10. The optic 242 includes a central zone 248 and a surrounding zone 250 that are similar to the zones 48, 50, respectively. The intraocular lens 240 is similar to the intraocular lens 40 with at least the exception that it includes an inner ring 246. At least a portion of the inner ring 246 is transparent and has a transmissivity of at least 80%, preferably at least 90% or even 95% or greater. The haptic 244 further comprises a plurality of arms 252 that connect the inner ring 246 with the peripheral portion 251. In the illustrated embodiment, there are eight arms 252; however, more or fewer arms may be used (e.g., 4 arms or 16 arms).

The inner ring 246 is configured to deform an optic 242 in response to an ocular force acting on a peripheral portion 251 of the haptic 244. The inner ring 246 is shown in the form of a contiguous ring in FIGS. 9 and 11. Alternatively, the inner ring 246 may be in the form of a broken ring with radial voids between ring segments, for example, with a radial void disposed between each of the arms 252. The peripheral portion 251 may be in the form of a continuous ring, as shown in the illustrated embodiment, or in the form of a broken ring. Either or both rings 246, 251 may have shapes that are not circular and may be shaped to distribute an ocular force about the optic 242 in a predetermined manner.

Various modified embodiments below are provided in which an arcuate member similar to the ring 246 is adapted to apply a non-uniform force to an optic to induce asymmetrical forces applied to an optic to produced an optical performance characteristic.

Figure 9:
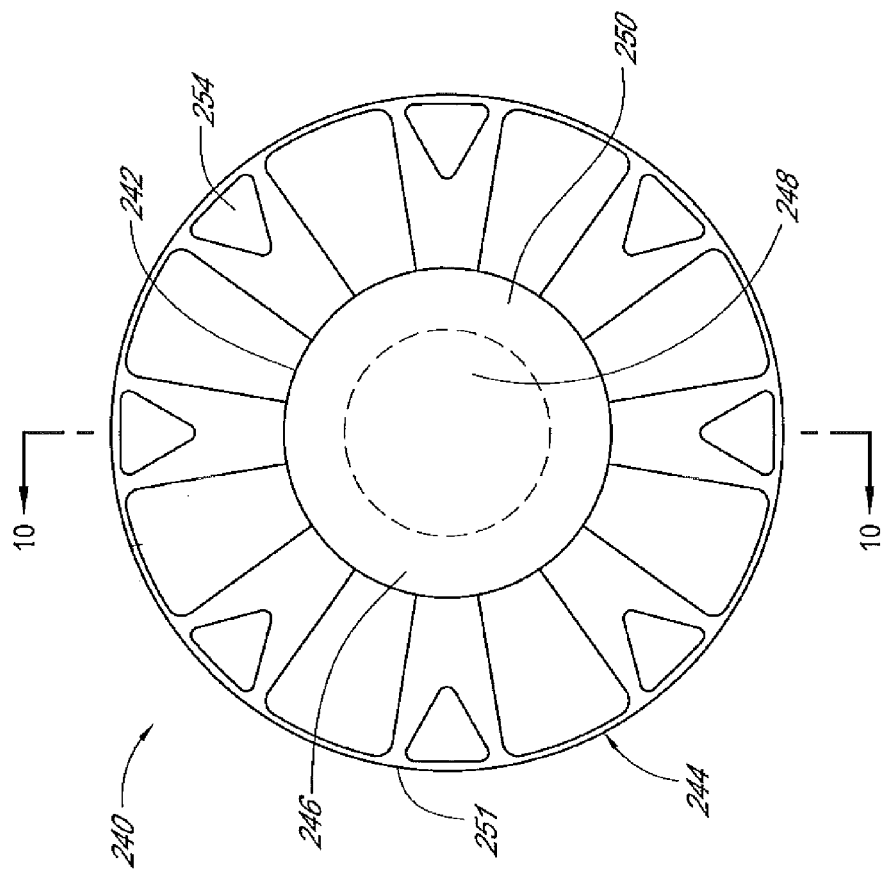
FIG. 9 is a front view of an intraocular lens according to a second embodiment.

The arms 252 may include void portions 254 configured to reduce the mass of the intraocular lens 240 and the haptic 244. Such reduction in mass may be utilized to allow the ocular force F to be more completely transmitted to the inner ring 246 and optic 242. The void portions may be triangular in shape, as illustrated in FIGS. 9 and 11, or may have some other shape (e.g., circular or rectangular) that may be selected to provide a desired mass reduction and/or distribution of forces on the inner ring 246 and/or adjustable optic 242.

Figure 10:
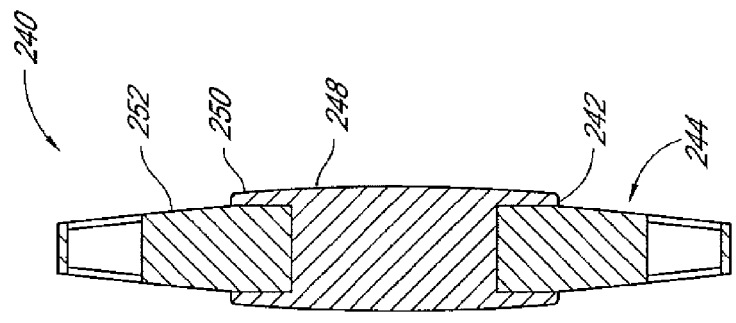
FIG. 10 is a cross-sectional view through the section 10-10 of FIG. 9.

The thickness along the optical axis OA of inner ring 246 (and/or of portions of the haptic 244 disposed within the adjustable optic 242) may be selected to control the amount and/or distribution of an ocular force acting on the intraocular lens 240. For example, in some embodiments, the performance (e.g., the change Diopter power of the intraocular lens 240 between accommodative and disaccommodative configurations) increases as the edge thickness increases. In such embodiments, other design constraints (e.g., optical performance or physical constraints of the eye) may, however, place an upper limit on the maximum optic edge thickness. In some embodiments, the ring portion 246 of the haptic 244 has a maximum axial thickness that is at least one half a maximum axial thickness of the central zone, as illustrated in FIG. 10. In other embodiments, the ring portion 246 of the haptic 244 has a maximum axial thickness that is at least 75% of a maximum axial thickness of the central zone. These and other predetermined relationships between axial thicknesses of the protruding portions of the haptic 244 and the axial thicknesses of the optic 242 may also be advantageously applied to other embodiments of the invention discussed or suggested herein. For example, the thickness of the haptic arms may be selected to control the amount and/or distribution of an ocular force acting on the optic 242. Also, where applicable, any of the features, limits, and so forth disclosed with regard to the intraocular lens 40 may also be applied to the intraocular lens 240.

2. Bag Filling Configurations

Figure 13:
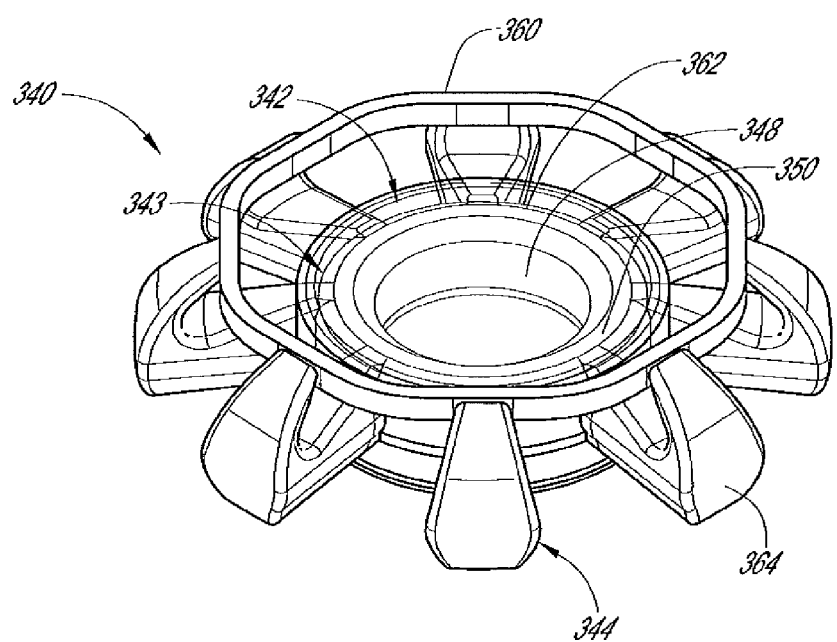
FIG. 13 is an isometric view of an intraocular lens according to a third embodiment.
Figure 14:
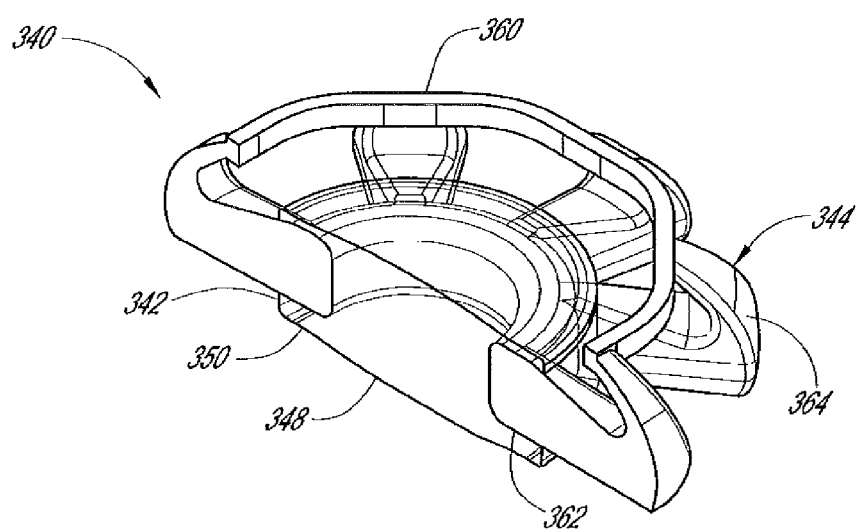
FIG. 14 is a cross-sectional isometric view of the intraocular lens of FIG. 13 showing a haptic segment operably coupled to an optic segment.
Figure 15:
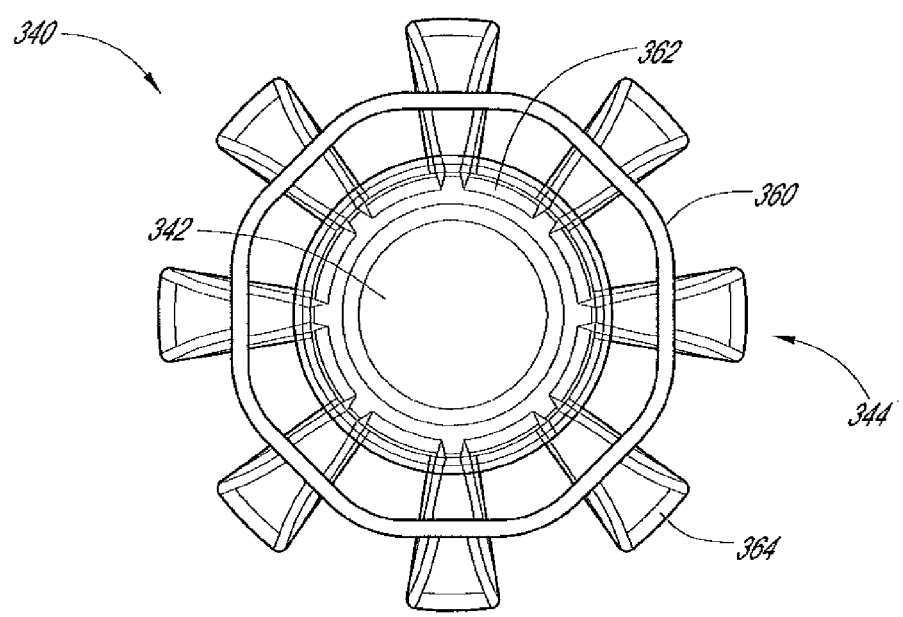
FIG. 15 is a front view of the intraocular lens shown in FIG. 13

Referring to FIGS. 13-15, an intraocular lens 340 comprising an adjustable optic 342 and a haptic 344 may be configured to have an accommodative bias when placed into the eye 10. The optic 342 includes a central zone 348 and a surrounding zone 350 that are similar to the zones 48, 50, respectively, of the previous embodiment. The haptic 344 comprises a plurality of arms connected together at their distal ends by an external ring 360 and at their proximal ends by an inner ring 362 disposed within the optic 342. In the illustrated embodiment, there are eight arms; however, more or fewer arms may be used. Similar to the intraocular lens 240, at least a portion of the ring 362 is transparent and has a transmissivity of at least about 80%, preferably at least 90% or even 95% or greater. Preferably, the refractive index of the inner ring is substantially equal to the refractive index of the adjustable optic 342.

The outer surface of the haptic 344 is configured to contact a relatively larger region of a capsular bag 18, for example, a region that extends beyond an equatorial region of the capsular bag 18. In the illustrated embodiment, the haptic comprises an outer surface 364 that is configured to conform to at least one of the anterior and posterior capsules of a capsular bag into which the intraocular lens is placed. The relatively large surface area of the outer surface 364 of the haptic 344 may be utilized to provide increased adhesion between the capsular bag and the intraocular lens 340.

Because of this increased adhesion, the intraocular lens 340 may be better suited for use as an accommodatively biased intraocular lens or other configurations where the intraocular lens is pulled outwardly by the capsular bag. In certain embodiments, a method implanting the intraocular lens 340 and providing accommodative vision is similar to that of the method 100, except that the intraocular lens 340 is placed into the eye in an accommodated configuration and adjusted to a disaccommodative configuration by using the walls of a capsular bag to pull radially outward on the inner ring 362 and the adjustable optic 342. Where applicable, any of the features, limits, and so forth disclosed with regard to the intraocular lenses 40, 240 may also be applied to the intraocular lens 340.

II. Intraocular Lenses with Enhanced Performance Through Asymmetric Loading

As discussed above, generally symmetric haptics can be used to provide accommodation and multiple foci. Further enhancement of performance can be obtained by asymmetric loading of an optic. Asymmetric loading can enhance performance by increasing the add power between unstressed and stressed states, compensate for aberrations due to asymmetry in the patient's anatomy, and/or exploit optical asymmetry to improve visual acuity.

A. Accommodating Intraocular Lenses Having Increased Add Power

FIGS. 16-22 illustrate further embodiments in which ocular force is concentrated in a particular region to enhance the add power in that region.

FIG. 16 shows an intraocular lens 400 having an optic 404 and a haptic 408. The optic 404 focuses light on the retina when disposed in the eye 10. In one embodiment, the intraocular lens 400 has an unstressed configuration and a stressed configuration. In the stressed configuration, ocular forces are transferred to the optic 404 asymmetrically through the haptic 408. Asymmetric force transfer can cause asymmetric deformation of the optic 404. Asymmetric deformation can produce a plurality of optical powers and/or aberrations, as discussed below.

In one variation, the optic 404 has a first zone 412 and a second zone 416 in the stressed configuration where the first zone 412 provides a distance vision power and the second zone 416 provides a near vision power. The near vision power is greater than the distance vision power. In one embodiment, the first zone 412 and the second zone 416 both have a distance vision power in the unstressed configuration. The intraocular lens 400 can be configured so that the first and second zones 412, 416 provide the same power in the unstressed state.

The second zone 416 preferably is an adjustable zone that can be adjusted through a range of optical powers when in a stressed state, e.g., subjected to a compressive ocular force. A maximum power of the second zone 416 when in a stressed state is greater than the distance vision power in first zone 412 when the optic is in the unstressed state. In some embodiments, the range of powers includes a near vision power, e.g., a power sufficient sufficient to bring into focus on the retina objects within 12 to 24 inches from the eye. The power of the first zone 412 in a stressed state can be the same as in the unstressed state or can vary in a range greater than the distance vision power.

Figure 17:
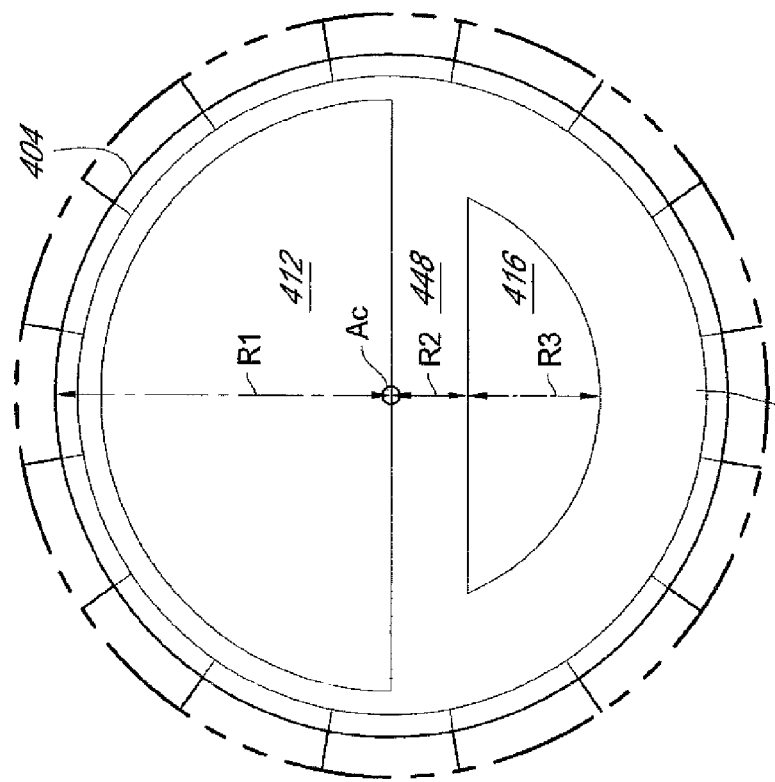
FIG. 17 is a partial view of the optical area of the intraocular lens of FIG. 16.

FIG. 17 shows that a central optical axis $A_C$ of the intraocular lens 400 intersects the first zone 412. The second zone 416 is adjacent the first zone 412 and off-set from the axis $A_C$. In some embodiments, the second zone 416 is smaller than the first zone 412, although other embodiments include a second zone that is similar in size to the first zone. The second zone 416 can be disposed in a region covering less than one-half of the surface area of the optic 404. In one embodiment, the second zone 416 has an arcuate or semi-circular configuration with a radial width $R_3$ less than a radius $R_1$ of the optic 404. The innermost edge of the radial span of the second zone 416 can be off-set form the center of the radius $R_1$ by a distance $R_2$. Preferably the innermost edge of the radial span of the second zone 416 is spaced from the center of the radius $R_1$ by an amount sufficient to permit the vision system of the patient to select between the regions 412, 416 depending on the position of the object to be viewed. The innermost edge of the radial span of the second zone 416 can be spaced apart from the location of the center of radius $R_1$ by at least about 30 percent of the diameter of the optic 404. In other embodiments, the second zone 416 extends up to a diameter of the optic 404 but may have a zone of greatest flexibility that is spaced radially from the diameter of the optic 404. In another embodiment, the first zone and second zone may be symmetrical arcuate segments which may be advantageous for a toric lens design.

FIG. 19A shows that the intraocular lens 400 is adapted to respond to ocular forces to adjust the power of the second zone 416 toward the near vision power. In particular, the solid line illustrates the power across the optic 404 in an unstressed state. As shown, the first zone 412 (between 0 and $R_1$) and the second zone 416 (between $R_2$ and $R_3$) each have distance vision power in the unstressed state. The dashed line shows that the first zone 412 (between 0 and $R_1$) has distance vision power and the second zone 416 (between $R_2$ and $R_3$) has near vision power in the stressed state. The difference between the power of the second zone 416 in the stressed state and the first zone 412 in the unstressed state can be 2 Diopters or more. In some embodiments, this difference, i.e., the "add power", can be 2-4 Diopters. In some embodiments, the add power can be 5 Diopters or more.

In one approach, the intraocular lens 400 is configured such that, when implanted in the patient, the second zone 416 is located below the first zone 412. For example, a particular diameter of the optic 404 is selected to be placed generally in the eye and the second zone 416 is below that diameter. In this context the terms "horizontally disposed" and "below" refers to the orientation when where the patient is upright.

The additional power of the second zone 416 results from a change in shape of the optic 404, e.g., of the second zone 416. The shape change is the result of asymmetric transfer of ocular force through the lens 400. Asymmetric force transfer is generally achieved through various configurations of the haptic 408, but could also be due to the configuration of the optic 404 as discussed below. In some embodiments, the haptic 408 also changes the shape of the first zone 412 but by a lesser amount than the second zone 416. In other embodiments, the ocular forces are asymmetrically applied to the optic to cause maximum add power in the first zone 412 and a lesser add power in the second zone 416, as discussed below.

In the embodiment of FIG. 16-19, the haptic 408 includes outer and inner members 432, 436. One or more of the inner and outer members 432, 436 can be annular, e.g., including rings or ring segments. The outer and inner members 432, 436 can be coupled together by a radially extending structure, such as by a plurality of arms 460 as discussed above. One technique for transferring force asymmetrically through the haptic 408 is through the configuration of the inner member 436. The inner member 436 can be adapted to asymmetrically transfer forces from the outer periphery of the haptic 408 to the optic 404. The inner member 436 can be configured to transfer more ocular force to a zone of the optic 404 for a desired optical effect. For example, the inner annular member 436 can be configured to act on a portion of the second zone 416 to cause the optical power of the zone 416 to vary through a range, as discussed above.

The inner member 436 can include a flexible portion 438 disposed adjacent to or inside at least the second zone 416 of the optic 404. In one variation the flexible portion 438 borders (e.g., at least partially surrounds) the second zone 416. The inner member 436 also includes a stiff portion 440 that is disposed adjacent to or inside the first zone 412. In one variation the stiff portion 440 at least partially surrounds (e.g., borders) the first zone 412. The flexible portion 438 can be made more flexible than the stiff portion 440 by manipulating the material properties.

For example, the material properties in the stiff and flexible portions 438, 440 can be different, e.g., higher modulus in the flexible region 438 and lower modulus in the stiff region 440. Techniques for varying modulus of a material are discussed in US Publication No. 2009-0163602, which is incorporated by reference in its entirety. The portion 438 can be made flexible by mechanical techniques, such as perforating or segmenting the portion 438. Other techniques for increasing or decreasing the stiffness of the stiff or flexible portions 438, 440 include changing the thickness. In one embodiment, the enhanced thickness is measured in a radial direction, e.g., perpendicular to the axis $A_C$. In one embodiment, the enhanced thickness is measured in a direction parallel to the axis $A_C$.

In one embodiment, the flexible portion 438 of the inner annular member 436 includes a ring segment subtending an arc of about 180 degrees between a first end 442 and a second end 444. In the embodiment of FIGS. 16-19, the first and second ends 442, 444 are connected by a transverse member 448 that extends across the optic 404. In one embodiment, both the flexible portion 438 and the transverse member 448 of the haptic 408 are disposed inside the optic 404. The transverse member 448 can be disposed between the first zone 412 and the second zone 416. In other embodiments, the first zone 412 and the second zone 416 are adjacent with no transverse member between them.

Figure 18:
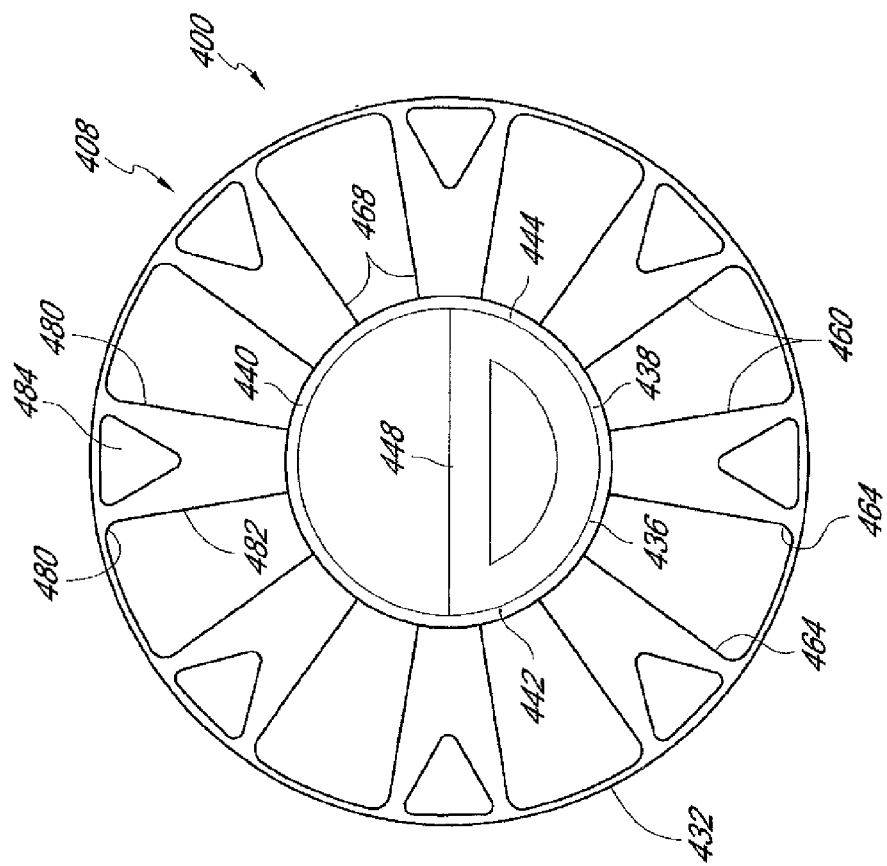
FIG. 18 is a front view of a haptic of the intraocular lens shown in FIG. 16.

The arms 460 include distal ends 464 coupled with the outer member 432, proximal ends 468 coupled with the inner member 436, and a length extending therebetween. FIG. 18 illustrate that the arms 460 can all have the same configuration. In addition, the arms 460 can be symmetrically disposed about the axis $A_C$. In other embodiments, the arms may be asymmetrically disposed about the axis $A_C$ in order to provide asymmetric forces on the optic. The inner and outer annular member 432, 436 are symmetric or asymmetric around the axis $A_C$.

FIG. 16A shows that the haptic 408 and the intraocular lens 400 have a substantially planar structure. For example, in one embodiment a plane extending through the outer member 432 and oriented perpendicular to the axis $A_C$ intersects the optic 404. In another embodiment, a plane extending through the outer member 432 and perpendicular to the axis $A_C$ intersects the inner member 436 and the optic 404. In another embodiment, a plane extending through a mid-point of the outer member 432 also extends through a mid-point of the inner annular member 436. In this context, the "mid-point" is measured in a direction parallel to the axis $A_C$.

Configuring the intraocular lens 400 in a generally planar arrangement has several advantages. First, if the intraocular lens 400 is placed in a capsular bag, the ocular forces are generally applied inwardly toward the axis $A_C$ and/or outwardly away from the axis $A_C$, e.g., along a plane perpendicular to the axis $A_C$ and intersecting the equator of the capsular bag. By placing the annular member 432 at the equator, and the arms 460 in the plane along which the ocular forces act, the intraocular lens maximizes compression of the optic 404. The in-plane transfer of forces through the arms 460 to the optic minimizes torque and maximizes deformation force to a portion of the optic 404, e.g., to the second zone 416.

In other embodiment similar to that of FIGS. 13-15, a plane perpendicular to the axis $A_C$ and intersecting the annular member 432 is disposed anterior to a plane perpendicular to the axis $A_C$ and intersecting the annular member 436. In such embodiments, the haptic 408 fills the evacuated capsular bag to a greater extent. Bag filling arrangements can be advantageous in some cases. For example, these arrangements prevent or substantially reduce a shrink-wrap effect that can occur in an evacuated capsular bag, which could result in compressive force being applied to the optic 404 along the direction of the axis $A_C$. Such forces could impede deformation of the optic 404. Also, if the haptic has a bag filling configuration, the surface area of contact between the haptic and the interior of the capsular bag is greater, e.g., because the surface area of the arms that engages the bag interior is greater. FIGS. 13-14 show, for example, that haptics with a bag filling arrangement extend radially outwardly to an outer surface configured to engage the capsular bag and anteriorly from this surface to a location anterior of the equator. Further, the annular member 432 can be configured to engage a posterior facing inside surface of an anterior aspect of the capsular bag, which can move in response to ocular forces on the capsular bag. Relative movement between the capsular bag and the annular member 432 can create a fulcrum effect, increasing the force applied to the optic 404. In bag filling variations, the annular member 432 need not be larger than the annular member 436. For example, the annular member 432 need not be partially or entirely located farther from the axis $A_C$ than is the annular member 436. Also, the annular member 432 could be disposed proximally of the optic 404. In this optic 404. In this arrangement, the annular member 432 would be configured to engage an anterior facing inside surface of a posterior aspect of the capsular bag. This arrangement could be advantageous in biasing the optic forward of the posterior aspect of the capsular bag to reduce the chance of subluxation. The annular member 432 could be configured with distinct edges that impede posterior capsule opacification.

In one embodiment, the haptic 408 includes eight arms 460 that extend between the inner and outer members 436, 432. The arrangement of the arms 460 and the inner and outer members 432, 436 can vary. FIG. 16 shows that three of the arms are coupled with the flexible portion 438 of the inner annular member 436 and three of the arms 460 are coupled with the stiff portion 440 of the inner annular member 436. Two of the arms 460 are coupled with both the stiff and flexible portions 438, 440. In order to increase the amount of force into any zone, the thickness of the arm 460 and/or material flexibility may be manipulated. Additionally, the thickness and/or material flexibility of any circumferential or surrounding member extending between arms (e.g., rings) may be changed in order to change the force applied to the optic. In other embodiments, the number of arms protruding into a particular zone may be varied in order to vary the force applied to the optic.

In one embodiment, the transverse member 448 and the flexible portion 438 of the inner member 436 surround the second zone 416. The area of the optic 404 that corresponds to the second zone 416 is smaller than the area of the first zone 412. In one embodiment, the second zone 416 is less than half of the surface area of the first zone 412. The first zone 412 may be fixed power or responsive to ocular forces to increase its power. A greater change in power results in the second zone 416 than in the first zone 412 because the area to be deformed in the second zone 416 is smaller, which results in higher pressure in the second zone 416 for a comparable force. This in conjunction with the flexible portion 438 allows for greater deformation and power change in the second zone 416. The second zone 416 may also be designed to result in little or now deformation if a stiff material (along with thicker design) prevents the second zone from transferring force. In such an embodiment, the first zone 412 may be comprised of a more flexible material such that the first zone 412 results in an increase in power due to deformation.

In some variations, the transverse member 448 is disposed inside a portion of the optic that does not change shape or power, but rather substantially retains the power of the first zone 412. FIG. 19A illustrates this feature in that the power between $R_1$ and $R_2$ in the stressed state (dashed line) is the same as in the unstressed state (solid line).

FIG. 19B illustrates the optical behavior of another arrangement in which the first zone 412 is more responsive to ocular forces than the second zone 416. By reducing the volume of material of portion 440, less ocular force is absorbed in deformation of the portion 440 and more of the force is available to deform the optic. In effect, the more flexible portion 440 may more efficiently transfers ocular force to the first zone 412 than is transferred by the stiff portion 438 to the second zone 416. Also, reinforcing a portion of the inner annular member 436 bordering the second zone 416 may isolate the second zone 416 from ocular forces transferred through the haptic 408. In such an arrangement, the first zone 412 will be more responsive to ocular forces to deform more, inducing a greater power add than the in the second zone 416.

The outer member 432 includes a continuous structure that entirely surrounds the optic 404. The outer member 432 is configured to engage or be disposed in an ocular structure, such as the capsular bag as discussed above. For example, the outer member 432 can be configured to be placed against an interior aspect of an evacuated capsular bag at the equator of the bag. In other embodiments, the outer member 432 is configured to be inserted into an intraocular lens holder, such as any of those described in U.S. Pat. No. 6,797,004 and in US Publication No. 2010-0094415, both of which are incorporated by reference in their entireties.

FIG. 18 shows that in one embodiment, the outer member 432 is a ring having an inner radius, an outer radius, and a radial thickness that is substantially constant thereround. In modified embodiments, the outer member 432 can include non-circular rings, oval or wavy structures, and/or a plurality of substantially straight segments. The outer member 432 also need not be continuous but rather can include a plurality of arcuate or linear segments with circumferential gaps therebetween.

Figure 20:
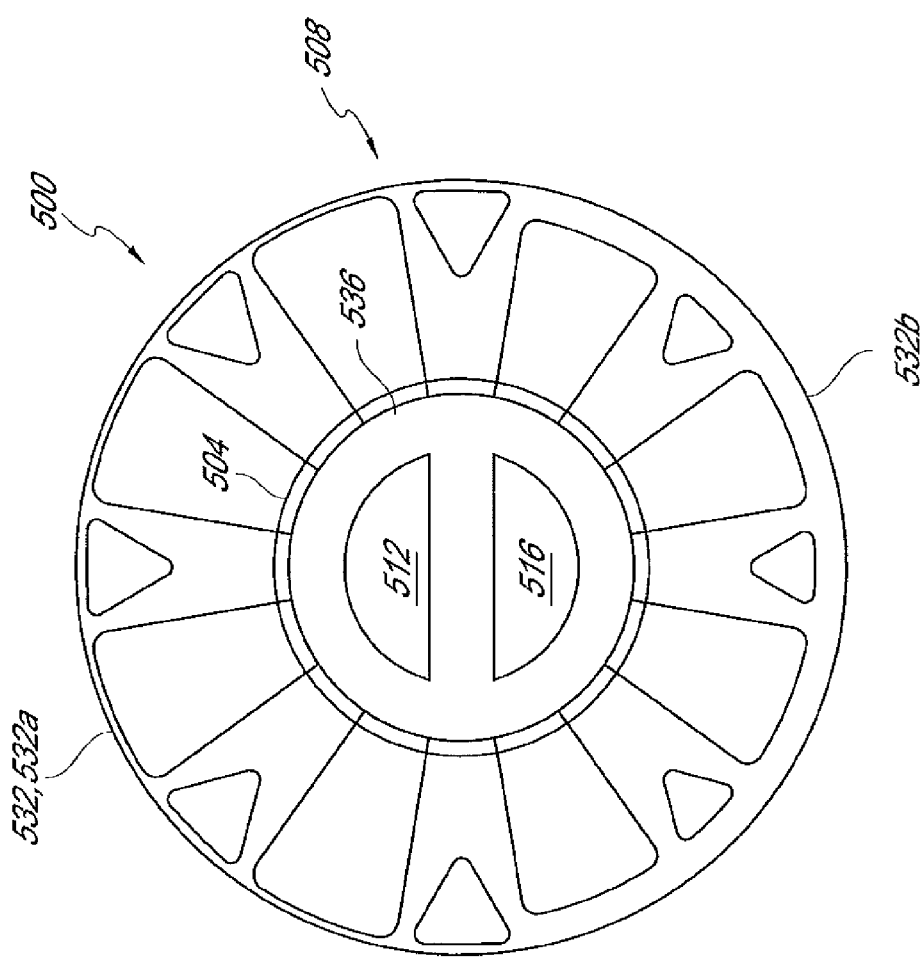
FIG. 20 is a front view of a variation of the intraocular lens of FIG. 16.

FIG. 20 illustrates an intraocular lens 500 similar to the lens 400, having a first zone 512 and a second zone 516 but where an outer member 532 thereof has a non-uniform force transfer configuration. The non-uniform force transfer configuration enables a haptic 508 of which the outer member 532 is a part to apply forces asymmetrically to an optic 504 of the lens 500. In some embodiments, the haptic 508 includes an inner member 536. In other embodiments, the haptic 508 can include cantilevered arms as in the embodiment of FIGS. 3-5. Non-uniform force transfer from the outer member 532 can induce different amounts of power add in different areas of the optic 504 to provide the benefits described herein.

The outer member 532 includes a non-uniform ring with a first portion 532a disposed about a distance power region and a second portion 532b disposed around a near power region. The first portion 532a is less stiff than the second portion 532b, such as by having less radial thickness. Other techniques discussed herein to make the first portion 532a less stiff than the second portion 532b could also employed in connection with the lens 500. By being stiffer, the second portion 532b is able to transfer more ocular force to the optic 504 than is transferred by the first portion 532a, producing a greater increase in the second zone 516 than would be provided in an intraocular lens having a constant stiffness outer member 532.

In variations of any of the intraocular lenses disclosed herein, the optic can comprise at least three zones. The zones can include zones similar to the first and second zones discussed above and a third zone having a range of powers greater than the distance vision power. The range of powers in the third zone can include an intermediate power, which is a maximum power that is less than the near vision power. In one arrangement, the outer member 532 is configured to induce at least the intermediate power in the third zone and the near vision power in the second zone. Such an arrangement may have the second zone with near vision as a concentric annular ring surrounding the optical axis. The third zone for intermediate vision may concentrically surround the first zone. The first zone with distance vision would lie outside and concentrically surround the third zone.

FIG. 18 shows that the arms 460 can be symmetrical, though other embodiments can have asymmetric configurations. The distal ends 464 of the arms have a forked configuration with two tapered legs 480 extending proximally to a waist portion 482. A void space 484 is disposed between the legs 480 and a segment of the outer member 432. The arms 460 are tapered from a waist portion 482 toward the inner member 436. The circumferential length of the proximal end 468 of each of the arms 460 is less than the circumferential length of the segment of the outer member 436 extending between the distal ends of the legs 480.

The complex geometry of the arms 460 provides a number of structural features that can be varied about the circumference of the haptic 408 to provide asymmetric force transfer capability about the optic 404 to provide accommodative compensation performance as desired. For example, the length and/or thickness of the arms 460 may be manipulated to vary the force provided to the optic 404.

Figure 21:
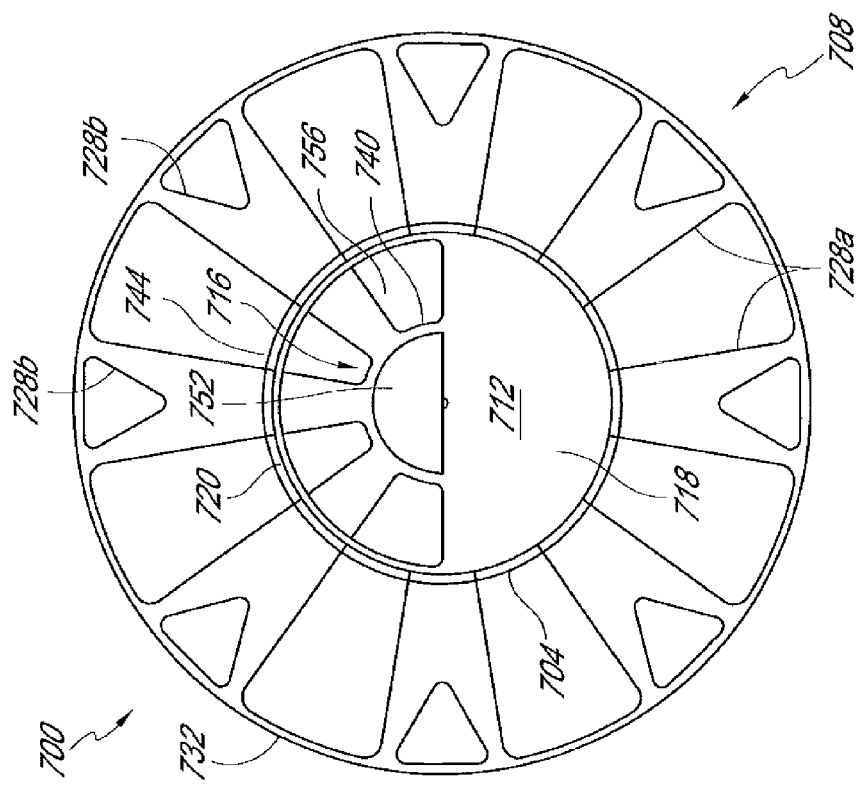
FIG. 21 is a plan view of another embodiment of an intraocular lens having a stiff sublayer disposed therein and a plurality of add power foci.

FIG. 21 illustrates an intraocular lens 700 that is similar to those hereinbefore described except as discussed below. The intraocular lens 700 includes an optic 704 and a haptic 708. The optic 704 has a fixed power region 712 and an add power region 716. The add power region 716 is flexible or deformable so that is power can be varied, as discussed above, at least up to a power sufficient for near vision.

The haptic 708 includes a stiff portion 718 configured to be disposed inside the fixed power region 712 and a deformable portion 720 configured to be disposed inside the add power region 716 of the optic 704. The stiff portion 718 can take any suitable form but preferably includes a rigid member, such as a rigid disk, that can be disposed within the fixed power region 712. The stiff portion 718 can include a substantially continuous solid member. The stiff portion 718 and the fixed power region 712 extend between a periphery of the optic 704 and a central zone of the optic. The fixed power region 712 covers a semi-circular portion of the optic 704 in the embodiment of FIG. 21.

The stiff portion 718 is coupled with the proximal ends of a plurality of arms 728a extending radially away from an outer periphery of the stiff portion 718 toward an outer periphery of the intraocular lens. An outer member 732 can be disposed at the outer periphery. The stiff portion 718 extends between proximal ends of at least some of the arms 728a.

The stiff portion 718 can be entirely encapsulated within the optic 704. In some embodiments, the stiff portion 718 is disposed beneath at least one of an anterior surface and a posterior surface of the optic 704 and thus may be referred to herein as a sublayer. The outer periphery of the stiff portion 718 is disposed closer to a central optical axis $A_C$ than is the outer periphery of the optic 704. In one embodiment, the stiff portion 718 has a posterior surface disposed anterior of the posterior surface of the optic 704. Also, the anterior surface of the stiff portion 718 can be disposed posterior of the anterior surface of the optic 704. The stiff portion 718 is configured to limit, e.g., substantially prevent, deformation of the optic 704 in the fixed power region 712.

The deformable portion 720 of the haptic 708 includes an inner member 740 and an intermediate member 744 disposed between the inner member and the outer periphery 732. The inner and intermediate members 740, 744 can be arcuate members, e.g., ring shaped. In one embodiment, the inner member 740 includes at least one ring segment disposed between adjacent arms 728b and at least one ring segment extending between an arm 728b and the stiff portion 718. The inner member 740 can comprise a plurality of ring segments connecting a plurality of arms 728b at their proximal ends. The inner member 740 can comprise a plurality of ring segments connecting a plurality of arms 728b to the stiff portion 718.

An inner add power region 752 is disposed between the inner arcuate member 740 and the fixed power region 712. The deformable portion 720 is adapted to increase the power of the add power region 752 by transferring ocular forces applied to the outer periphery 720 to the add power region.

In one embodiment an outer add power region 756 is defined between the inner add power region 752 and the intermediate arcuate member 744. The outer add power region is an annular segment extending circumferentially from a first end adjacent to the fixed power region 712 on one side of the optic 704 to a second adjacent to the fixed power region 712 on an opposite side of the optic 704. The outer add power region 756 can include one or a plurality of regions defined between the members 740, 744 and the arms 728b. The outer add power region 756 also can include one or a plurality of regions defined between the arcuate member 740, 744, one of the arms 728b, and an edge of the stiff portion 718.

The intermediate arcuate member 744 transfers a portion of the ocular force to the outer add power region 756 producing an add power. The add power of the outer add power region can be a different power from that of the inner add power region 752. In particular, the outer add power region 756 can provide an intermediate power zone giving the patient the ability to select between viewing intermediate objects and near objects without changing the accommodated state of the intraocular lens 700.

The gaps between the arms 728b, the arcuate member 740, 744, and the stiff portion 718 can be filled with a deformable material. The material can be the same as or different than the material disposed over the stiff portion 718 of the haptic 708. For example, a suitable gel can be disposed in these regions. A suitable gel is one that maintains an optical surface but is deformable under the loads applied by the eye and transferred through the deformable portion 720 of the haptic 708. Suitable gels include hydrophilic based and silicone based gels.

Figure 22:
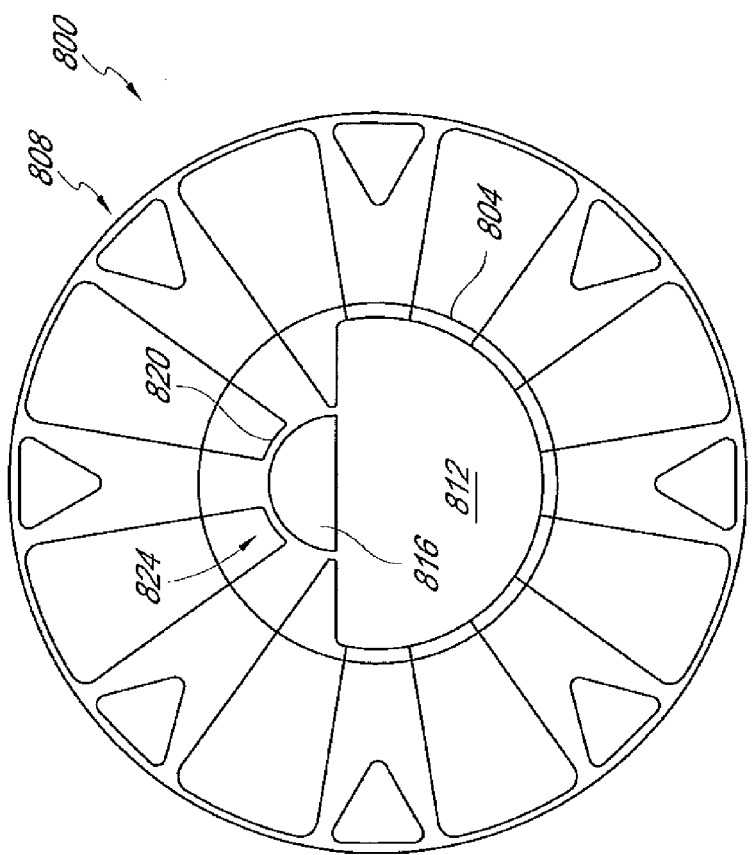
FIG. 22 is a plan view of another embodiment of an intraocular lens having a stiff sublayer and an add power region spaced from the geometric center of the lens.

FIG. 22 illustrates another intraocular lens 800 that is similar to that of FIG. 21 except as set forth below. The lens 800 includes an optic 804 and a haptic 808. More than half of the optic 804 comprises a fixed power region 812 and less than half of the optic comprises an adjustable add power region 816. In one variation, the add power region 816 is disposed within an arcuate member 820. The add power region 816 can comprise a portion of the optic 804 where deformation is concentrated to enhance the add power of the optic 804. The add power region 816 can be semi-circular with a radius that is less than the radius of the optic 804. The add power region 816 can have a geometric center that is off-set from the geometric center of the optic 804.

A peripheral area 824 surrounding one side of the add power region 816 can be configured to have negligible change in shape and power, for example matching the shape and power of the fixed power region 812.

In the embodiments of FIGS. 21-22, the arms coupled with the more deformable portion of the respective haptic are longer. The arms in these portions extend further into their respective optics to position the application of force closer to the zone to be modified to the higher power. This feature, in addition to being coupled with a more flexible haptic construction, enables these embodiments to enhanced add power of the intraocular lenses.

B. Intraocular Lenses Having Asymmetric Force Transfer

The intraocular lenses discussed below are configured to correct for a patient's asymmetric optical aberrations and optionally provide accommodation.

Forces in the eye, such as within the capsular bag as applied by the ciliary muscles, are believed to be symmetric about the equator of the capsular bag. Asymmetric aberrations can be treated by configuring an intraocular lens to transfer these symmetric ocular forces asymmetrically to an optic or by configuring an optic to respond asymmetrically to a uniform force. These configurations can create or increase asymmetry of an optical surface in a stressed or unstressed state to decrease an asymmetric aberration. These configurations can induce, increase, or decrease the asymmetry of an asymmetric optical surface in a stressed or unstressed state to provide or eliminate an extended depth of focus in one of these states.

If the forces around the capsular bag are not uniform, asymmetric transfer of force within the intraocular lens can provide some of the same advantages or can be used to compensate for force asymmetry in the patient's anatomy.

Among the asymmetric effects that can be induced in the intraocular lens or optic are differential bending along different axes or chords of the optic. In general asymmetric bending can be provided by varying mechanical properties of the haptic, the optic, or both the haptic and optic asymmetrically.

Figure 23B:
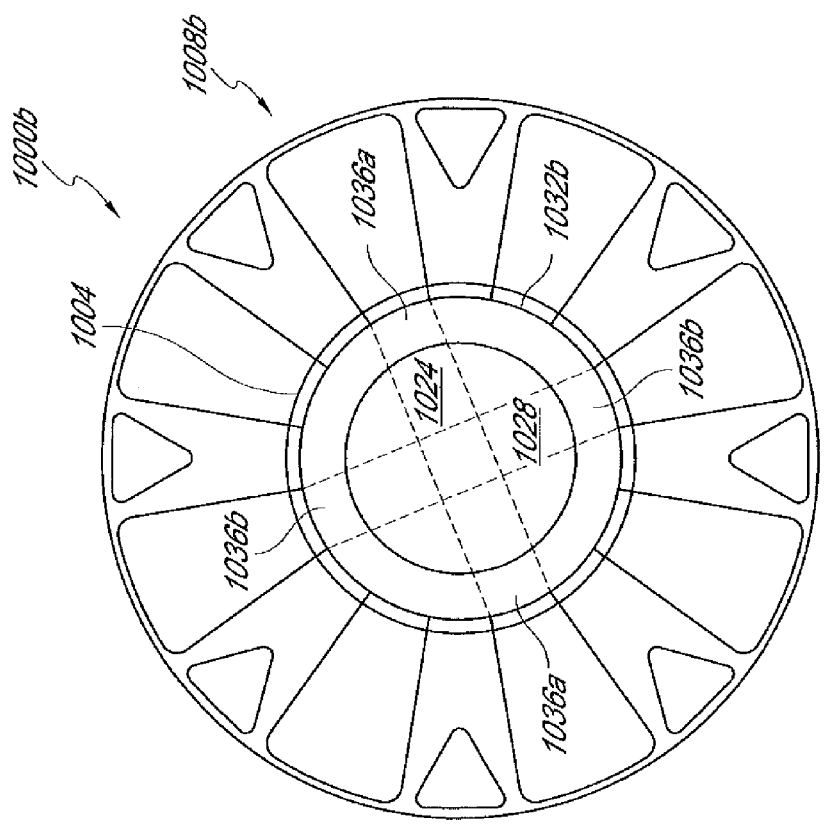
FIGS. 23A-23F illustrate a variety of intraocular lens structures that asymmetrically respond to symmetrical ocular forces.
Figure 23A:
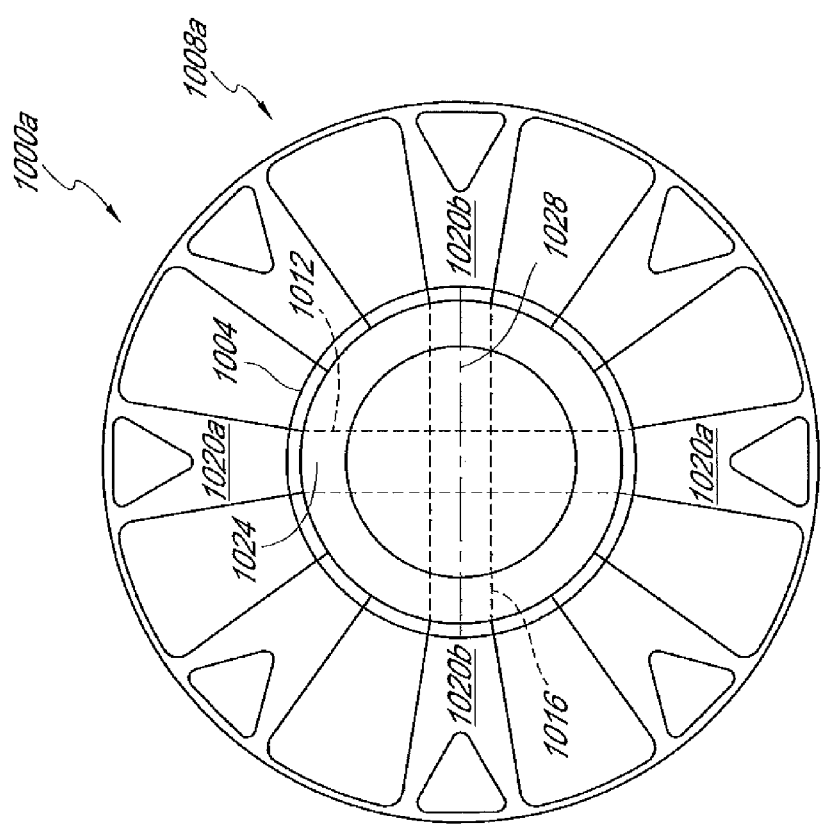

FIG. 23A shows an intraocular lens 1000a including an optic 1004 and a haptic 1008. The optic 1004 is adapted to be deformed when subjected to a compressive ocular force transferred through the haptic 1008a. The haptic 1008a is adapted to apply different forces to different portions of the optic 1004 in response to a uniform annular compressive ocular force, e.g., as applied by the ciliary muscles through the capsular bag. The haptic 1008a is configured to apply a first compressive force to a first portion 1012 of the optic 1004 and a second compressive force to a second portion 1016 of the optic 1004. The first and second portions 1012, 1016 of the optic 1004 are deformed, e.g., to change power, when subjected to the compressive ocular force. The intraocular lens may be configured such that the first portion 1012 of the optic changes power by a greater amount than more than the second portion 1016.

In one variation, a first portion of the haptic 1008a applies more force to the optic 1004 than a second portion of the haptic 1008a. The haptic 1008a can include a plurality of arms 1020a and 1020b disposed around the optic 1004. In one embodiment, one or both of a first pair of haptic arms 1020a is configured to apply a greater force to the optic 1004 than one or both of a second pair of haptic arms 1020b. Where the pair of haptic arms 1020a is disposed on opposing sides of the optic 1004 along a first transverse portion 1024 (e.g., a diameter or chord), a change in curvature along the first transverse portion 1024 due to the application of a uniform ocular force can be greater than the change in curvature along a second transverse portion 1028 that extends between the second pair of haptic arms 1020b. This configuration produces more change in curvature along the first transverse portion 1024 than along the second transverse portion 1028 in response to a uniform ocular force. This can be used to eliminate astigmatism in an eye system (including the intraocular lens) at least when the optic 1004 is in the deformed state when the intraocular lens 1000a is properly oriented in the eye. If astigmatism is more pronounced in distance vision, the intraocular lens 1000 can be configured to be asymmetric when unstressed and to deform to a symmetrical configuration by transferring the symmetric force asymmetrically to the optic 1004, for example by configuring the pairs of arms

1020*a*, 1020*b* to differentially apply force. In some embodiments, astigmatism may be enhanced to increase depth of focus.

FIG. 23B shows that the haptic 1008*a* can include an inner member 1032*b* through which force is applied to a central zone of the optic 1004. Some embodiments are similar to those of FIGS. 3-5, having cantilevered arms 1020*a*, 1020*b*, which would provide free ends at the proximal portion of the arms, e.g., ends not connected to each other by other portions of the haptic.

A variety of techniques can be used to cause the first pair of haptic arms 1020*a* to apply a greater force even when a uniform compressive force is applied to the intraocular lens 1000*a*. For example, the one or more bulk properties of the first pair of haptic arms 1020*a* can be different from the bulk properties of the second pair of haptic arms 1020*b*. Modulus of elasticity is one property that relates to the force transfer capability. Alternatively, the mechanical configuration of the arms can be modified. The first pair of haptic arms 1020*a* can be modified by any suitable technique so that they are more compressible along their longitudinal axis compared to the second pair of haptic arms 1020*b*. Or, the second pair of haptic arms 1020*b* can be made less flexible. Other mechanical techniques for modifying the force transfer capability of the haptic arms 1020*a* and/or 1020*b* include modifying the thickness of the haptic arms 1020*a* and/or 1020*b* or pre-stressing the haptic arms 1020*a* and/or 1020*b*. In addition, the haptic arms 1020*a* and/or 1020*b* may be curved in order to apply force to various areas of the optic depending on the type of asymmetric compression sought.

FIG. 23B shows an intraocular lens 1000*b* having a haptic 1008*b* in which all of the arms have the same force transfer properties but an inner portion of the haptic is configured to transfer a non-uniform force to the optic 1004 when the intraocular lens 1000*b* is subject to a uniform ocular force.

The haptic 1008*b* includes an inner member 1032*b* that is coupled with proximal ends of the arms 1020*a* and 1020*b*. The inner member 1032*b* can be a ring as discussed above. In one variation, the inner annular member 1032*b* has a plurality of segments that respond differently to the application of an ocular (e.g., compressive) force. A first pair of segments 1036*a* of the inner annular member 1032*b* can be disposed on opposite sides of the first transverse portion 1024 and a second pair of segments 1036*b* can be disposed on opposite sides of the second transverse portion 1028. The first pair of segments 1036*a* can be configured to apply a greater force to the optic 1004 along the first transverse portion 1024 than is applied along the second transverse portion 1028 by the second pair of segments 1036*b*.

Figure 23D:
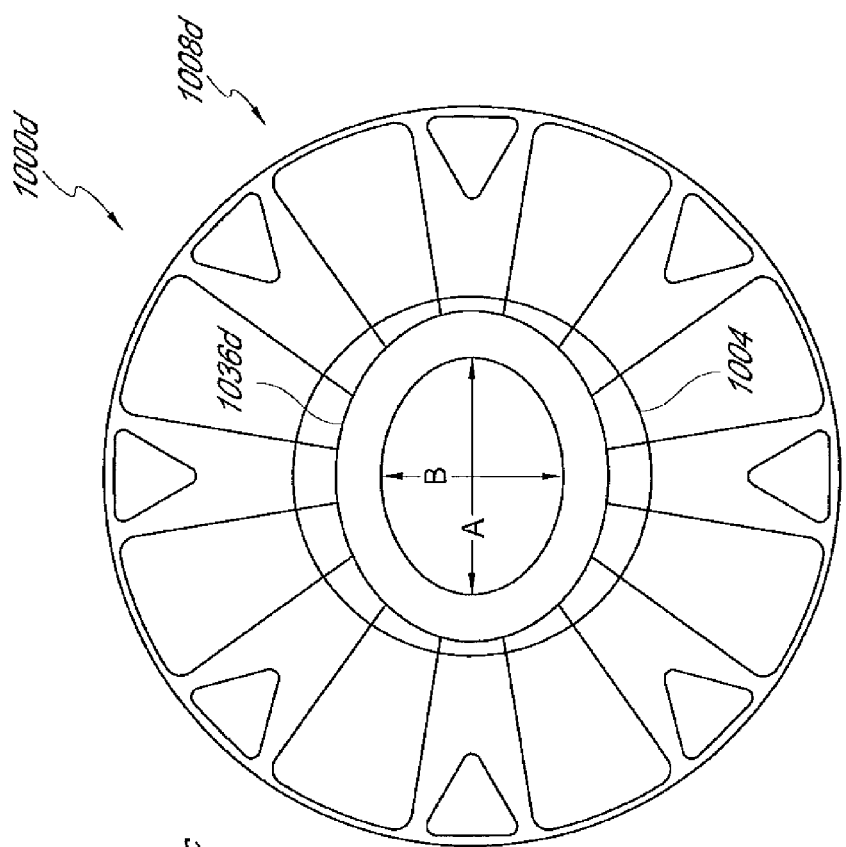

The segments 1036*a*, 1036*b* can be portions of a continuous inner member 1032*b* as illustrated in FIG. 23B. In other embodiments, the segments 1036*a*, 1036*b* have free ends disposed circumferentially spaced apart from each other. The segments 1036*a*, 1036*b* can be separated from adjacent portions of the inner member 1032*b* by void spaces, as illustrated in FIG. 23E to enhance the differential force transfer capability of the segments 1036*a*, 1036*b*.

A variety of techniques can be used to cause the first pair of segments 1036*a* to apply a greater force even when a uniform compressive force is applied to the intraocular lens 1000*b* as detailed herein.

Figure 23C:
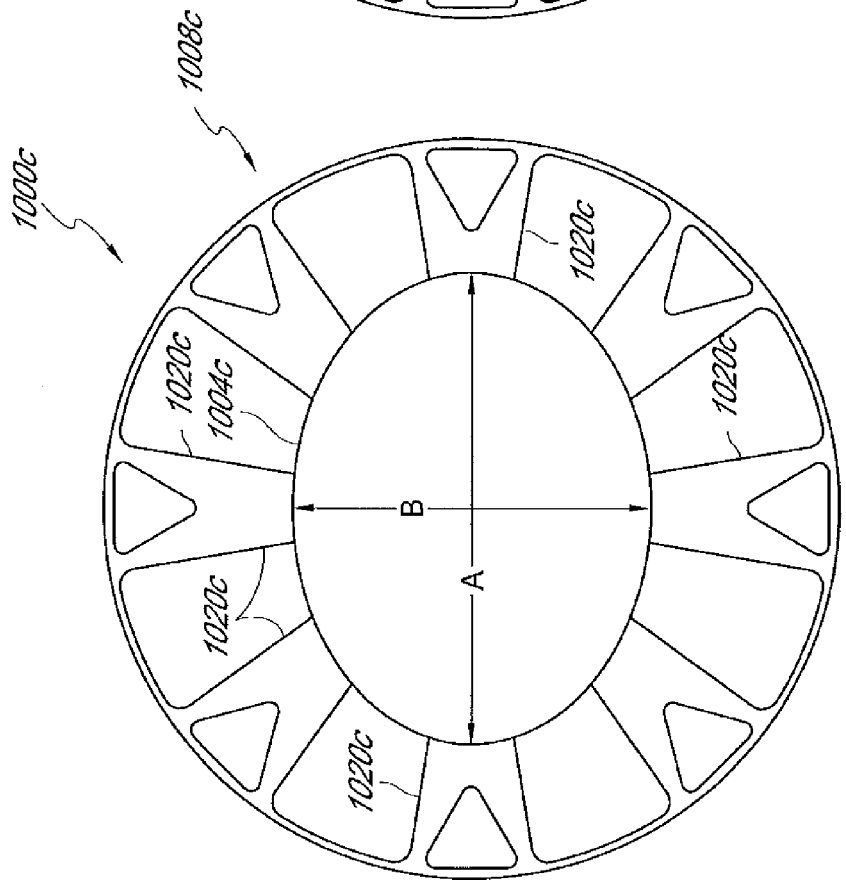

FIG. 23C illustrates another embodiment of an intraocular lens 1000*c* that responds asymmetrically to a symmetrical ocular force. An optic 1004*c* is provided that is asymmetric in at least one respect such that it is more responsive to a compressive force in one portion than in another portion. For example, the optic 1004*c* can have any combination of underformed surfaces, such as spherical or symmetrical in planes containing a central optical axis $A_C$, but be asymmetric in a plane perpendicular to the axis $A_C$. In particular, the optic 1004*c* can be oval or other non-symmetrical shape in a plan transverse to the axis $A_C$. If the bulk material properties do not vary within the optic 1004*c*, the oval shape is more compressible along the minor axis B than along the major axis A because the distance from the application of force to the center of the optic is less than it is along the major axis A. This arrangement can create address asymmetric aberrations, such as by creating or eliminating an astigmatic effect.

FIG. 23C shows that a haptic 1008*c* coupled with the optic 1004*c* may incorporate arms 1020*c* of different lengths in order to couple with the periphery of the optic 1004*c*. In one embodiment, the different length of the arms 1020*c* enables the haptic 1008*c* to maintain a generally circular outer member 1032 while the optic is oval shaped or elongated in at least one axis. Although the arms 1020*c* are shown coupling generally to the peripheral side surface of the optic 1004*c*, this disclosure also contemplates that the arms 1020*c* could protrude into the optic 1004*c* as in the embodiment of FIGS. 3-5. In one variation, the haptic 1008*c* has substantially uniform arms, some of which protrude by a greater amount into the optic 1004*c*. In another variation, the arms can be coupled at their proximal ends by an inner member such as is described above.

Figure 23F:
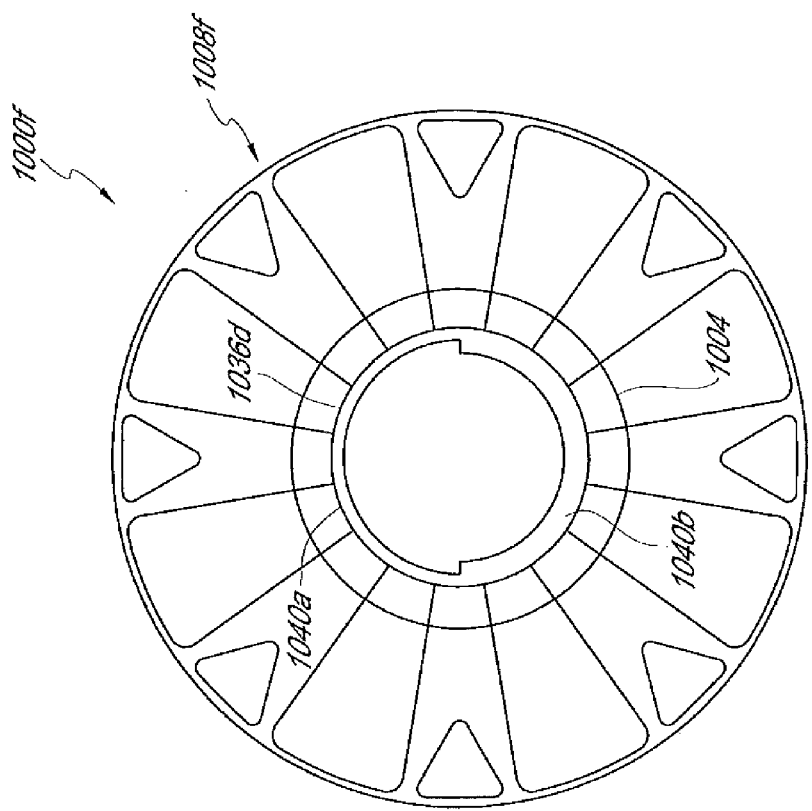
Figure 23E:
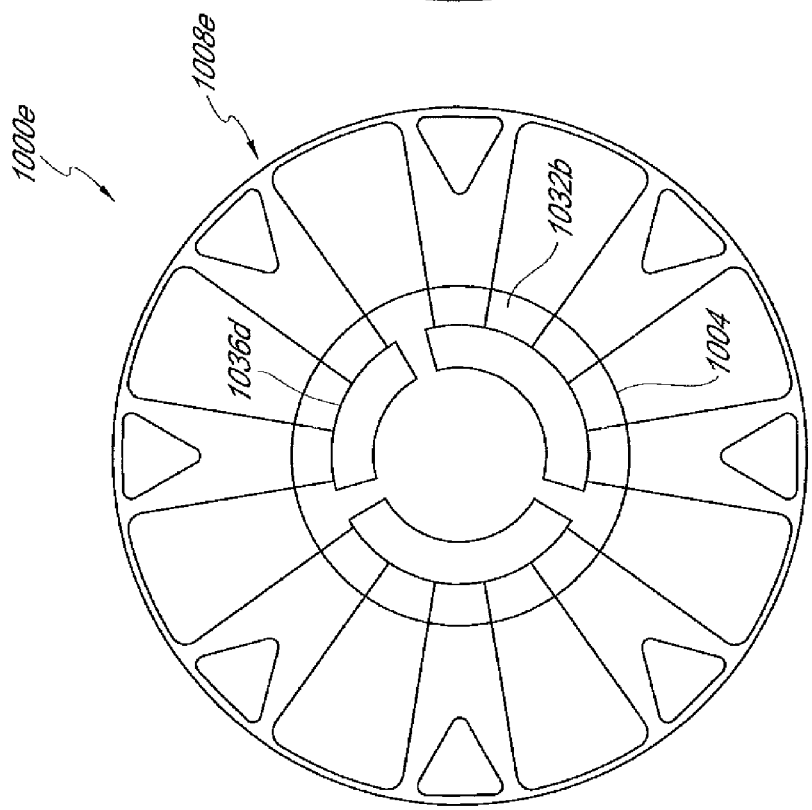

FIG. 23D shows another embodiment of the intraocular lens 1000*d* in which a portion of a haptic 1008*d* disposed inside the optic 1004 is asymmetric to induce asymmetry in the deformation of the optic 1004 in response to uniform ocular forces. The intraocular lens 1000*d* includes an inner member 1036*d* disposed therein that is asymmetric, for example having an oval or other elongated arcuate shape. The inner member 1036*d* has a first segment along the major axis A and a second segment along the minor axis B. The second segment is better able to bend at its midpoint than is the first segment if the inner member 1036*d* is otherwise uniform. Also, the distance from the application of force along the mid-point of the second segment to the center of the optic is less than the distance from the application of force at the mid point of the first segment to the center of the optic. As a result, the second segment is more effective at deforming the optic 1004 along the minor axis of the inner member 1036*d* than is the first segment along the major axis of the inner member 1036*d* such that asymmetry in the optic can be induced. In some embodiments, the inner member 1036*d* may have indentations to vary the location of force applied to the optic, or may even be separated and thus not continuous as illustrated in FIG. 23E. Additionally, the inner member 1036*d* may vary in thickness such that a first segment 1040*a* has a different radial thickness than the radial thickness of a second segment 1040*b* as illustrated in FIG. 23F. An intraocular lens similar to the intraocular lens 1000*f* illustrated in FIG. 23F having an inner member 1036*d* that has a variable thickness in the radial direction can be useful in tonic lenses that can correct for astigmatism in addition to myopia or hyperopia. In various embodiments, the inner member 1036*d* can have three regions, each region having a different thickness instead of two regions with different thickness. Such intraocular lenses may be useful to induce or correct an asymmetric aberration.

Figure 24A:
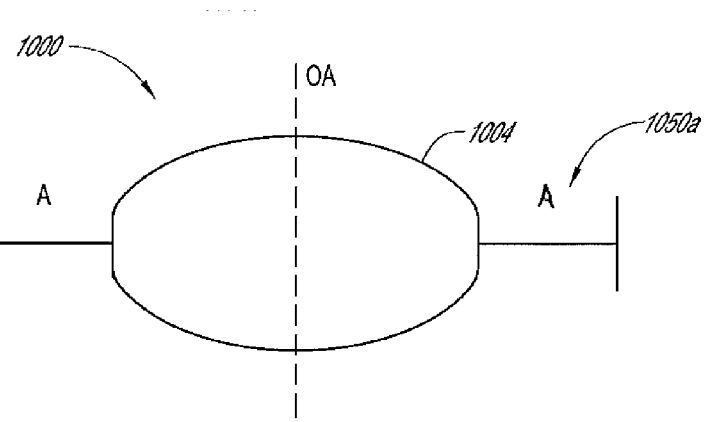
FIGS. 24A-24C illustrate an intraocular lens structure that asymmetrically responds to symmetrical ocular forces.
Figure 24B:
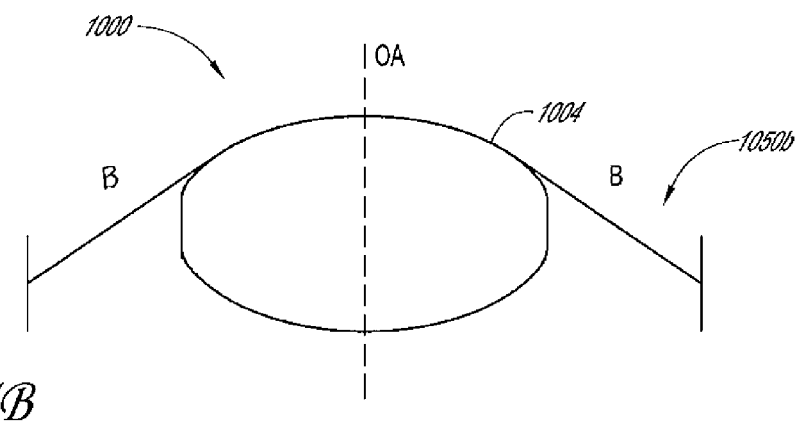
Figure 24C:
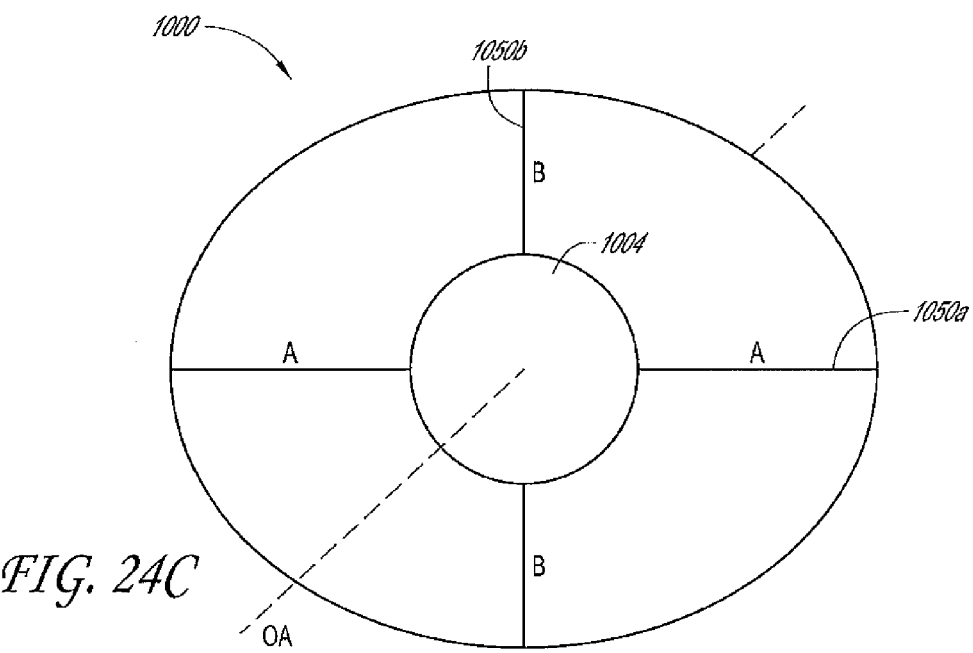

FIGS. 24A-24C show an embodiment 1000 where asymmetric vaulting or tilting may occur based on the location of the attachment of the haptic arm 1050*a* and 1050*b* to the optic 1004. FIGS. 24A and 24B shows cross-sectional views of the intraocular lens including the optical axis (OA) of the optic 1004. As shown in FIGS. 24A and 24B, haptic arms 1050*a* along major axis A are connected to the equatorial plane of optic 1004 (for example at the mid-point between the anterior and posterior surfaces of the optic 1004), while the haptic arms 1050b along the minor axis B attach to the optic 1004 in a plane away from the equatorial plane of the optic 1004. For example, the haptic arms 1050b can attach proximal to the anterior surface or the posterior surface of the optic 1004. Under the influence of an ocular force, the haptic arms 1050a may be more effective to provide compressive forces along the axis A such that the optic 1004 is deformed (e.g. bulged or flattened). Under the influence of an ocular force, the haptic arms 1050b may be more effective to vault or move the optic along a direction parallel to the optical axis OA. The combination of deformation and vaulting may result in asymmetric accommodation.

The description of the invention and its applications as set forth herein is illustrative and is not intended to limit the scope of the invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intraocular lens, comprising:
   an optic comprising a first zone having a distance vision power and a second zone being adjustable through a range of powers greater than the distance vision power; and
   a haptic comprising:
     an outer annular member;
     an inner annular member comprising a ring segment with a first end and a second end, wherein the first end and the second end is connected by a transverse member, wherein the transverse member connects the first end and the second end and is disposed between the first zone and the second zone; and
     a plurality of arms extending between the inner and outer annular members;
   wherein the intraocular lens is adapted to respond to ocular forces to adjust the power of the second zone.

2. The intraocular lens of claim 1, wherein the inner annular member comprises a first annular portion having a first stiffness and a second annular portion having a second stiffness, the second annular portion bounding a portion of the second zone.

3. The intraocular lens of claim 1, wherein the intraocular lens is reinforced in the first zone such that power increasing deformation is concentrated in the second zone.

4. The intraocular lens of claim 1, wherein a portion of the first zone bordering the second zone maintains the distance vision power when the power of the second zone is increased.

5. The intraocular lens of claim 1, wherein the outer annular member comprises a first portion disposed about a distance power region and a second portion disposed around a near power region, the first portion adapted to transfer a lesser amount of ocular force to the optic than the second portion.

6. The intraocular lens of claim 1, wherein the outer annular member is configured to transfer ocular forces in a manner that induces the power in at least the second zone toward a near vision power.

7. The intraocular lens of claim 1, wherein some of the plurality of arms include voids.

8. The intraocular lens of claim 1, wherein the outer annular member is spaced apart from the optic by the plurality of arms along a direction perpendicular to the optical axis.

9. The intraocular lens of claim 1, wherein the outer annular member comprises a continuous ring adapted to be disposed at the equator of a capsular bag and the inner annular member comprises a continuous ring adapted to be disposed inside the optic.

10. The intraocular lens of claim 1, wherein the second zone is adapted to provide at least 2 Diopters of add power.

* * * * *